(12) United States Patent
Chang

(10) Patent No.: US 10,736,812 B2
(45) Date of Patent: Aug. 11, 2020

(54) SYSTEM AND METHOD FOR SLOWING DOWN DEGENERATION OF CENTRAL NERVOUS SYSTEM CAUSED BY PARKINSON'S DISEASE

(71) Applicant: Wen-Chieh Chang, Taichung (TW)

(72) Inventor: Wen-Chieh Chang, Taichung (TW)

( * ) Notice: Subject to any disclaimer, the term of this patent is extended or adjusted under 35 U.S.C. 154(b) by 708 days.

(21) Appl. No.: 15/289,133

(22) Filed: Oct. 8, 2016

(65) Prior Publication Data

US 2017/0172842 A1 Jun. 22, 2017

(30) Foreign Application Priority Data

Dec. 18, 2015 (TW) .............................. 104142685 A

(51) Int. Cl.
*A61N 1/36* (2006.01)
*A61H 23/02* (2006.01)
*A61N 1/04* (2006.01)
*A61N 5/06* (2006.01)

(52) U.S. Cl.
CPC .......... *A61H 23/02* (2013.01); *A61H 23/0236* (2013.01); *A61N 1/0456* (2013.01); *A61N 1/36025* (2013.01); *A61N 5/0618* (2013.01); *A61N 5/0622* (2013.01); *A61H 2201/1628* (2013.01); *A61H 2201/5005* (2013.01); *A61N 2005/0652* (2013.01)

(58) Field of Classification Search
CPC .................... A61H 2201/5002; A61N 1/36025
See application file for complete search history.

*Primary Examiner* — Alyssa M Alter

(57) ABSTRACT

A system and method for slowing down degeneration of central nervous system caused by Parkinson's disease, which comprises an energy wave generator has an energy wave's frequency control mode. The energy wave's frequency control mode includes multiple controls for acting the energy wave generator to generate and emit energy waves each with a corresponding energy density. The energy density is calculated by a corresponding base frequency, a sweep bandwidth of the corresponding base frequency, an emission rate and a total time of emission in a duty cycle, so that the energy waves with the corresponding energy densities effecting on the body of animals or human to slow down degeneration of central nervous system caused by Parkinson's disease.

11 Claims, 11 Drawing Sheets

| Order | Ori. Fn | Duty | Pulse Rate | Time | Program Time (min, sec) Signal Type | | | | | Width | Total Time | Energy Density | 176 SUM | | | filter | Lower limit | Upper limit | 3.5 <Lower limit | 3.5 >Upper limit |
|---|---|---|---|---|---|---|---|---|---|---|---|---|---|---|---|---|---|---|---|---|
| n | Fo(hz) | D(%) | P(hz) | T(sec) | SF(1) | SDC(2) | SH(3) | SC(4) | SH(5) | m | TT(sec) | ED | Norm | ED | Aveage | | | | | |
| 1 | 1 | 70 | 1 | 30 | 1 | | | | | 0 | 30 | 1.34 | 0.8% | 1.34 | 1.34 | 1 | 0.67 | 1.68 | -2.16 | 4.84 |
| 2 | 2 | 70 | 1 | 30 | 1 | | | | | 0 | 30 | 1.63 | 0.9% | 1.63 | 1.63 | 1 | 0.82 | 2.04 | -1.87 | 5.13 |
| 3 | 3 | 70 | 1 | 30 | 1 | | | | | 0 | 30 | 1.81 | 1.0% | 1.81 | 1.81 | 1 | 0.90 | 2.26 | -1.69 | 5.31 |
| 4 | 4 | 70 | 1 | 30 | 1 | | | | | 0 | 30 | 1.93 | 1.1% | 1.93 | 1.93 | 1 | 0.96 | 2.41 | -1.57 | 5.43 |
| 5 | 5 | 70 | 1 | 30 | 1 | | | | | 0 | 30 | 2.03 | 1.1% | 2.03 | 2.03 | 1 | 1.01 | 2.53 | -1.47 | 5.53 |
| 6 | 6 | 70 | 1 | 30 | 1 | | | | | 0 | 30 | 2.10 | 1.2% | 2.10 | 2.10 | 1 | 1.05 | 2.63 | -1.40 | 5.60 |
| 7 | 7 | 70 | 1 | 30 | 1 | | | | | 0 | 30 | 2.17 | 1.2% | 2.17 | 2.17 | 0 | 0.00 | 0.00 | -1.33 | 5.67 |
| 8 | 8 | 70 | 1 | 30 | 1 | | | | | 0 | 30 | 2.23 | 1.3% | 2.23 | 2.23 | 0 | 0.00 | 0.00 | -1.27 | 5.73 |
| 9 | 10 | 70 | 1 | 30 | 1 | | | | | 0 | 30 | 2.32 | 1.3% | 2.32 | 2.32 | 0 | 0.00 | 0.00 | -1.18 | 5.82 |
| 10 | 12 | 70 | 1 | 30 | 1 | | | | | 0 | 30 | 2.40 | 1.4% | 2.40 | 2.40 | 0 | 0.00 | 0.00 | -1.10 | 5.90 |
| 11 | 13 | 70 | 1 | 30 | 1 | | | | | 0 | 30 | 2.44 | 1.4% | 2.44 | 2.44 | 1 | 1.22 | 3.05 | -1.06 | 5.94 |
| 12 | 15 | 70 | 1 | 30 | 1 | | | | | 0 | 30 | 2.50 | 1.4% | 2.50 | 2.50 | 1 | 1.25 | 3.12 | -1.00 | 6.00 |
| 13 | 20 | 70 | 1 | 30 | 1 | | | | | 0 | 30 | 2.62 | 1.5% | 2.62 | 2.62 | 1 | 1.31 | 3.28 | -0.88 | 6.12 |
| 14 | 25 | 70 | 1 | 30 | 1 | | | | | 0 | 30 | 2.72 | 1.5% | 2.72 | 2.72 | 1 | 1.36 | 3.40 | -0.78 | 6.22 |
| 15 | 30 | 70 | 1 | 30 | 1 | | | | | 0 | 30 | 2.80 | 1.6% | 2.80 | 2.80 | 1 | 1.40 | 3.50 | -0.70 | 6.30 |
| 16 | 35 | 70 | 1 | 30 | 1 | | | | | 0 | 30 | 2.87 | 1.6% | 2.87 | 2.87 | 0 | 0.00 | 0.00 | -0.63 | 6.37 |
| 17 | 40 | 70 | 1 | 30 | 1 | | | | | 0 | 30 | 2.92 | 1.7% | 2.92 | 2.92 | 0 | 0.00 | 0.00 | -0.58 | 6.42 |
| 18 | 50 | 70 | 1 | 30 | 1 | | | | | 0 | 30 | 3.02 | 1.7% | 3.02 | 3.02 | 0 | 0.00 | 0.00 | -0.48 | 6.52 |
| 19 | 60 | 70 | 1 | 30 | 1 | | | | | 0 | 30 | 3.10 | 1.8% | 3.10 | 3.10 | 0 | 0.00 | 0.00 | -0.40 | 6.60 |
| 20 | 80 | 70 | 1 | 30 | 1 | | | | | 0 | 30 | 3.23 | 1.8% | 3.23 | 3.23 | 0 | 0.00 | 0.00 | -0.27 | 6.73 |
| 21 | 90 | 70 | 1 | 30 | 1 | | | | | 0 | 30 | 3.28 | 1.9% | 3.28 | 3.28 | 1 | 1.64 | 4.10 | -0.22 | 6.78 |
| 22 | 100 | 70 | 1 | 30 | 1 | | | | | 0 | 30 | 3.32 | 1.9% | 3.32 | 3.32 | 1 | 1.66 | 4.15 | -0.18 | 6.82 |
| 23 | 130 | 70 | 1 | 30 | 1 | | | | | 0 | 30 | 3.44 | 2.0% | 3.44 | 3.44 | 0 | 0.00 | 0.00 | -0.06 | 6.94 |
| 24 | 200 | 70 | 1 | 30 | 1 | | | | | 0 | 30 | 3.62 | 2.1% | 3.62 | 3.62 | 1 | 1.81 | 4.53 | 0.12 | 7.12 |
| 25 | 300 | 70 | 1 | 30 | 1 | | | | | 0 | 30 | 3.80 | 2.2% | 3.80 | 3.80 | 1 | 1.72 | 4.30 | 0.30 | 7.30 |
| 26 | 500 | 70 | 1 | 30 | 1 | | | | | 0 | 30 | 4.02 | 2.3% | 4.02 | 4.02 | 0 | 0.00 | 0.00 | 0.52 | 7.52 |
| 27 | 10000 | 70 | 1 | 30 | 1 | | | | | 0 | 30 | 4.32 | 2.5% | 4.32 | 4.32 | 0 | 0.00 | 0.00 | 0.82 | 7.82 |
| 28 | 3000 | 70 | 1 | 22 | 1 | | | | | 0 | 22 | 5.19 | 2.9% | 5.19 | 5.19 | 0 | 0.00 | 0.00 | 1.69 | 8.69 |
| 29 | 3000 | 70 | 1 | 25 | 1 | | | | | 0 | 25 | 4.72 | 2.7% | 4.72 | 4.72 | 0 | 0.00 | 0.00 | 1.22 | 8.22 |
| 30 | 1864 | 70 | 1 | 2 | 1 | | | | 5 | 4 | 18 | 5.33 | 3.0% | 5.33 | 5.33 | 1 | 2.21 | 5.53 | 1.83 | 8.83 |
| 31 | 1357 | 70 | 1 | 28 | 1 | | | | | 0 | 28 | 4.42 | 2.5% | 4.42 | 4.42 | 1 | 2.17 | 5.44 | 0.92 | 7.92 |
| 32 | 1062 | 70 | 1 | 30 | 1 | | | | | 0 | 30 | 4.35 | 2.5% | 4.35 | 4.35 | 1 | 2.15 | 5.37 | 0.85 | 7.85 |
| 33 | 880 | 70 | 1 | 32 | 1 | | | | | 0 | 32 | 4.29 | 2.4% | 4.29 | 4.29 | 1 | 2.14 | 5.36 | 0.79 | 7.79 |
| 34 | 787 | 70 | 1 | 35 | 1 | | | | | 0 | 35 | 4.29 | 2.4% | 4.29 | 4.29 | 0 | 0.00 | 0.00 | 0.79 | 7.79 |
| 35 | 727 | 70 | 1 | 35 | 1 | | | | | 0 | 35 | 4.25 | 2.4% | 4.25 | 4.25 | 0 | 0.00 | 0.00 | 0.75 | 7.75 |
| 36 | 720 | 70 | 1 | 2 | 1 | | | 4 | | 0 | 30 | 5.36 | 3.0% | 5.36 | 5.36 | 0 | 0.00 | 0.00 | 1.86 | 8.86 |
| 37 | 650 | 70 | 1 | 38 | 1 | | | | | 0 | 38 | 4.24 | 2.4% | 4.24 | 4.24 | 0 | 0.00 | 0.00 | 0.74 | 7.74 |
| 38 | 625 | 70 | 1 | 4 | 1 | 2 | | | | 7 | 32 | 5.05 | 2.9% | 5.05 | 5.05 | 1 | 1.98 | 4.94 | 1.55 | 8.55 |
| 39 | 600 | 70 | 1 | 4 | 1 | 2 | | | | 7 | 32 | 5.03 | 2.9% | 5.03 | 5.03 | 1 | 1.85 | 4.63 | 1.53 | 8.53 |
| 40 | 520 | 70 | 1 | 8 | 1 | 2 | | | | 3 | 32 | 4.67 | 2.6% | 4.67 | 4.67 | 1 | 2.07 | 5.17 | 1.17 | 8.17 |
| 41 | 304 | 70 | 1 | 42 | 1 | | | | | 0 | 42 | 3.95 | 2.2% | 3.95 | 3.95 | 1 | 1.98 | 4.94 | 0.45 | 7.45 |
| 42 | 160 | 70 | 1 | 45 | 1 | | | | | 0 | 45 | 3.70 | 2.1% | 3.70 | 3.70 | 1 | 1.85 | 4.63 | 0.20 | 7.20 |
| 43 | 144 | 70 | 1 | 15 | 1 | 2 | | | | 2 | 45 | 4.13 | 2.3% | 4.13 | 4.13 | 1 | 2.07 | 5.17 | 0.63 | 7.63 |
| 44 | 125 | 70 | 1 | 8 | 1 | 2 | | | | 4 | 40 | 4.24 | 2.4% | 4.24 | 4.24 | 0 | 0.00 | 0.00 | 0.74 | 7.74 |
| 45 | 95 | 70 | 1 | 45 | 1 | | | | | 0 | 45 | 3.48 | 2.0% | 3.48 | 3.48 | 0 | 0.00 | 0.00 | -0.02 | 6.98 |
| 46 | 73 | 70 | 1 | 10 | 1 | | | | | 0 | 10 | 2.71 | 1.5% | 2.71 | 2.71 | 0 | 0.00 | 0.00 | -0.79 | 6.21 |
| 47 | 20 | 70 | 1 | 22 | 1 | | | | | 0 | 22 | 2.49 | 1.4% | 2.49 | 2.49 | 0 | 0.00 | 0.00 | -1.01 | 5.99 |
| 48 | 10 | 70 | 1 | 22 | 1 | | | | | 0 | 22 | 2.19 | 1.2% | 2.19 | 2.19 | 0 | 0.00 | 0.00 | -1.31 | 5.69 |
| 49 | 9 | 70 | 1 | 24 | 1 | | | | | 0 | 24 | 2.18 | 1.2% | 2.18 | 2.18 | 1 | 1.09 | 2.73 | -1.32 | 5.68 |
| 50 | 7 | 70 | 1 | 32 | 1 | | | | | 0 | 32 | 2.20 | 1.2% | 2.20 | 2.20 | 1 | 1.10 | 2.75 | -1.30 | 5.70 |
| 51 | 6 | 70 | 1 | 34 | 1 | | | | | 0 | 34 | 2.16 | 1.2% | 2.16 | 2.16 | 1 | 1.08 | 2.70 | -1.34 | 5.66 |
| 52 | 5 | 70 | 1 | 35 | 1 | | | | | 0 | 35 | 2.09 | 1.1% | 2.09 | 2.09 | 1 | 1.05 | 2.61 | -1.41 | 5.59 |
| 53 | 4 | 70 | 1 | 36 | 1 | | | | | 0 | 36 | 2.01 | 1.1% | 2.01 | 2.01 | 1 | 1.00 | 2.51 | -1.49 | 5.51 |
| 54 | 4 | 70 | 1 | 36 | 1 | | | | | 0 | 36 | 2.01 | 1.1% | 2.01 | 2.01 | 1 | 1.00 | 2.51 | -1.49 | 5.51 |
| 55 | 1 | 70 | 1 | 42 | 1 | | | | | 0 | 42 | 1.48 | 0.8% | 1.48 | 1.48 | 1 | 0.74 | 1.85 | -2.02 | 4.98 |

FIG.11

| Order | Ori. Fn | Duty | Pluse Rate | Time | Program Time (min, sec) Signal Type | | | | | Width | Total Time | Energy Density | 176 SUM | | | filter | Lower limit | Upper limit | 3.5 <Lower limit | 3.5 >Upper limit |
|---|---|---|---|---|---|---|---|---|---|---|---|---|---|---|---|---|---|---|---|---|
| n | Fo(hz) | D(%) | P(hz) | T(sec) | SF(1) | SD(2) | SI(3) | SC(4) | SE(5) | m | TT(sec) | ED | Norm | ED | Aveage | | | | | |
| 1 | 1 | 70 | 1 | 40 | 1 | | | | | 0 | 40 | 1.46 | 0.8% | 1.46 | 1.46 | 1 | 0.73 | 1.83 | -2.04 | 4.96 |
| 2 | 2 | 70 | 1 | 40 | 1 | | | | | 0 | 40 | 1.76 | 0.9% | 1.76 | 1.76 | 1 | 0.88 | 2.19 | -1.74 | 5.26 |
| 3 | 3 | 70 | 1 | 40 | 1 | | | | | 0 | 40 | 1.93 | 1.0% | 1.93 | 1.93 | 1 | 0.96 | 2.41 | -1.57 | 5.43 |
| 4 | 4 | 70 | 1 | 40 | 1 | | | | | 0 | 40 | 2.05 | 1.1% | 2.05 | 2.05 | 1 | 1.03 | 2.57 | -1.45 | 5.55 |
| 5 | 5 | 70 | 1 | 40 | 1 | | | | | 0 | 40 | 2.15 | 1.1% | 2.15 | 2.15 | 1 | 1.07 | 2.69 | -1.35 | 5.65 |
| 6 | 6 | 70 | 1 | 40 | 1 | | | | | 0 | 40 | 2.23 | 1.2% | 2.23 | 2.23 | 1 | 1.11 | 2.78 | -1.27 | 5.73 |
| 7 | 7 | 70 | 1 | 40 | 1 | | | | | 0 | 40 | 2.29 | 1.2% | 2.29 | 2.29 | 0 | 0.00 | 0.00 | -1.21 | 5.79 |
| 8 | 8 | 70 | 1 | 40 | 1 | | | | | 0 | 40 | 2.35 | 1.2% | 2.35 | 2.35 | 0 | 0.00 | 0.00 | -1.15 | 5.85 |
| 9 | 10 | 70 | 1 | 40 | 1 | | | | | 0 | 40 | 2.45 | 1.3% | 2.45 | 2.45 | 0 | 0.00 | 0.00 | -1.05 | 5.95 |
| 10 | 12 | 70 | 1 | 40 | 1 | | | | | 0 | 40 | 2.53 | 1.3% | 2.53 | 2.53 | 0 | 0.00 | 0.00 | -0.97 | 6.03 |
| 11 | 13 | 70 | 1 | 40 | 1 | | | | | 0 | 40 | 2.56 | 1.3% | 2.56 | 2.56 | 0 | 0.00 | 0.00 | -0.94 | 6.06 |
| 12 | 15 | 70 | 1 | 40 | 1 | | | | | 0 | 40 | 2.62 | 1.4% | 2.62 | 2.62 | 1 | 1.28 | 3.20 | -0.88 | 6.12 |
| 13 | 20 | 70 | 1 | 40 | 1 | | | | | 0 | 40 | 2.75 | 1.4% | 2.75 | 2.75 | 1 | 1.31 | 3.28 | -0.75 | 6.25 |
| 14 | 25 | 70 | 1 | 40 | 1 | | | | | 0 | 40 | 2.85 | 1.5% | 2.85 | 2.85 | 1 | 1.37 | 3.44 | -0.65 | 6.35 |
| 15 | 30 | 70 | 1 | 40 | 1 | | | | | 0 | 40 | 2.92 | 1.5% | 2.92 | 2.92 | 1 | 1.42 | 3.56 | -0.58 | 6.42 |
| 16 | 35 | 70 | 1 | 40 | 1 | | | | | 0 | 40 | 2.99 | 1.6% | 2.99 | 2.99 | 1 | 1.46 | 3.66 | -0.51 | 6.49 |
| 17 | 40 | 70 | 1 | 15 | 1 | | | | | 0 | 15 | 2.62 | 1.4% | 2.62 | 2.62 | 0 | 0.00 | 0.00 | -0.88 | 6.12 |
| 18 | 50 | 70 | 1 | 15 | 1 | | | | | 0 | 15 | 2.72 | 1.4% | 2.72 | 2.72 | 0 | 0.00 | 0.00 | -0.78 | 6.22 |
| 19 | 60 | 70 | 1 | 15 | 1 | | | | | 0 | 15 | 2.80 | 1.5% | 2.80 | 2.80 | 0 | 0.00 | 0.00 | -0.70 | 6.30 |
| 20 | 80 | 70 | 1 | 15 | 1 | | | | | 0 | 15 | 2.92 | 1.5% | 2.92 | 2.92 | 0 | 0.00 | 0.00 | -0.58 | 6.42 |
| 21 | 90 | 70 | 1 | 15 | 1 | | | | | 0 | 15 | 2.98 | 1.5% | 2.98 | 2.98 | 1 | 1.49 | 3.72 | -0.52 | 6.48 |
| 22 | 100 | 70 | 1 | 15 | 1 | | | | | 0 | 15 | 3.02 | 1.6% | 3.02 | 3.02 | 1 | 1.51 | 3.78 | -0.48 | 6.52 |
| 23 | 130 | 70 | 1 | 15 | 1 | | | | | 0 | 15 | 3.14 | 1.6% | 3.14 | 3.14 | 1 | 1.57 | 3.92 | -0.36 | 6.64 |
| 24 | 200 | 70 | 1 | 15 | 1 | | | | | 0 | 15 | 3.32 | 1.7% | 3.32 | 3.32 | 1 | 1.66 | 4.15 | -0.18 | 6.82 |
| 25 | 300 | 70 | 1 | 15 | 1 | | | | | 0 | 15 | 3.50 | 1.8% | 3.50 | 3.50 | 0 | 0.00 | 0.00 | 0.00 | 7.00 |
| 26 | 500 | 70 | 1 | 15 | 1 | | | | | 0 | 15 | 3.72 | 1.9% | 3.72 | 3.72 | 0 | 0.00 | 0.00 | 0.22 | 7.22 |
| 27 | 1000 | 70 | 1 | 15 | 1 | | | | | 0 | 15 | 4.02 | 2.1% | 4.02 | 4.02 | 0 | 0.00 | 0.00 | 0.52 | 7.52 |
| 28 | 6000 | 70 | 1 | 90 | 1 | | | | | 0 | 90 | 5.58 | 2.9% | 5.58 | 5.58 | 0 | 0.00 | 0.00 | 2.08 | 9.08 |
| 29 | 5000 | 70 | 1 | 90 | 1 | | | | | 0 | 90 | 5.50 | 2.9% | 5.50 | 5.50 | 0 | 0.00 | 0.00 | 2.00 | 9.00 |
| 30 | 4334 | 70 | 1 | 3 | | | | 4 | | 5 | 33 | 6.04 | 3.1% | 6.04 | 6.04 | 0 | 0.00 | 0.00 | 2.54 | 9.54 |
| 31 | 2890 | 70 | 1 | 3 | | | | 4 | | 5 | 33 | 5.87 | 3.0% | 5.87 | 5.87 | 1 | 2.93 | 7.33 | 2.37 | 9.37 |
| 32 | 1422 | 70 | 1 | 3 | | | | 4 | | 5 | 33 | 5.56 | 2.9% | 5.56 | 5.56 | 1 | 2.78 | 6.95 | 2.06 | 9.06 |
| 33 | 1131 | 70 | 1 | 3 | | | | 4 | | 5 | 33 | 5.46 | 2.8% | 5.46 | 5.46 | 1 | 2.73 | 6.82 | 1.96 | 8.96 |
| 34 | 878 | 70 | 1 | 3 | | | | 4 | | 5 | 33 | 5.35 | 2.8% | 5.35 | 5.35 | 1 | 2.67 | 6.69 | 1.85 | 8.85 |
| 35 | 840 | 70 | 1 | 3 | | | | 4 | | 5 | 33 | 5.33 | 2.8% | 5.33 | 5.33 | 0 | 0.00 | 0.00 | 1.83 | 8.83 |
| 36 | 820 | 70 | 1 | 3 | | | | 4 | | 5 | 33 | 5.32 | 2.8% | 5.32 | 5.32 | 0 | 0.00 | 0.00 | 1.82 | 8.82 |
| 37 | 739 | 70 | 1 | 3 | | | | 4 | | 5 | 33 | 5.27 | 2.7% | 5.27 | 5.27 | 0 | 0.00 | 0.00 | 1.77 | 8.77 |
| 38 | 719 | 70 | 1 | 3 | | | | 4 | | 5 | 33 | 5.26 | 2.7% | 5.26 | 5.26 | 0 | 0.00 | 0.00 | 1.76 | 8.76 |
| 39 | 693 | 70 | 1 | 3 | | | | 4 | | 5 | 33 | 5.25 | 2.7% | 5.25 | 5.25 | 0 | 0.00 | 0.00 | 1.75 | 8.75 |
| 40 | 658 | 70 | 1 | 3 | | | | 4 | | 5 | 33 | 5.22 | 2.7% | 5.22 | 5.22 | 0 | 0.00 | 0.00 | 1.72 | 8.72 |
| 41 | 611 | 70 | 1 | 3 | | | | 4 | | 5 | 33 | 5.19 | 2.7% | 5.19 | 5.19 | 1 | 2.60 | 6.49 | 1.69 | 8.69 |
| 42 | 573 | 70 | 1 | 3 | | | | 4 | | 5 | 33 | 5.16 | 2.7% | 5.16 | 5.16 | 1 | 2.58 | 6.45 | 1.66 | 8.66 |
| 43 | 527 | 70 | 1 | 3 | | | | 4 | | 5 | 33 | 5.13 | 2.7% | 5.13 | 5.13 | 1 | 2.56 | 6.41 | 1.63 | 8.63 |
| 44 | 470 | 70 | 1 | 3 | | | | 4 | | 5 | 33 | 5.08 | 2.6% | 5.08 | 5.08 | 0 | 0.00 | 0.00 | 1.58 | 8.58 |
| 45 | 442 | 70 | 1 | 3 | | | | 4 | | 5 | 33 | 5.05 | 2.6% | 5.05 | 5.05 | 0 | 0.00 | 0.00 | 1.55 | 8.55 |
| 46 | 312 | 70 | 1 | 3 | | | | 4 | | 5 | 33 | 4.90 | 2.5% | 4.90 | 4.90 | 0 | 0.00 | 0.00 | 1.40 | 8.40 |
| 47 | 228 | 70 | 1 | 3 | | | | 4 | | 5 | 33 | 4.76 | 2.5% | 4.76 | 4.76 | 0 | 0.00 | 0.00 | 1.26 | 8.26 |
| 48 | 231 | 70 | 1 | 3 | | | | 4 | | 5 | 33 | 4.77 | 2.5% | 4.77 | 4.77 | 0 | 0.00 | 0.00 | 1.27 | 8.27 |
| 49 | 171 | 70 | 1 | 3 | | | | 4 | | 5 | 33 | 4.64 | 2.4% | 4.64 | 4.64 | 1 | 2.32 | 5.80 | 1.14 | 8.14 |
| 50 | 132 | 70 | 1 | 3 | | | | 4 | | 5 | 33 | 4.53 | 2.3% | 4.53 | 4.53 | 1 | 2.26 | 5.66 | 1.03 | 8.03 |

FIG. 12

SYSTEM AND METHOD FOR SLOWING DOWN DEGENERATION OF CENTRAL NERVOUS SYSTEM CAUSED BY PARKINSON'S DISEASE

BACKGROUND OF THE INVENTION

1. Fields of the invention

The present invention relates to a system and method for slowing down degeneration of central nervous system caused by Parkinson's disease, and more particularly, to a technology for controlling and emitting energy waves to improve the symptoms of Parkinson's disease.

2. Descriptions of Related Art

Human life and the elderly population drastically increase because of the advances of technologies, most countries have entered into aging societies now, but unfortunately the number of Parkinson's disease has largely and continuously increased relatively, and the required medical treatments and health cares also have formed significant burdens of the societies. According to the current medical researches, the Parkinson's disease is a disease cause by the rapid deterioration of the basal ganglia and substantia nigra of brain cells. In short, Parkinson's disease is mainly due to the human brain can't produce enough nerve guides (Dopamine) and the raising of the anticholinergic effects.

Generally, the human brain needs the dopamine to direct the activities of muscles. When the dopamine is lack, various kinds of barriers of physical activities will produce. Substantia nigra is for manufacturing dopamine neurons, and dopamine neurons are important components of the basal ganglia. The basal ganglia are complex circuit buried deeply in the brain, which is responsible for fine-tuning and coordinating movement. When dopamine neurons in the substantia nigra are in the beginning of death, although the brain can't make up these dead cells and are still able to function properly, however, when the number of these special cells death more than half once, including the thalamus, basal ganglia and cerebral cortex can't be united and harmoniously functioned, and result in triggering actions such as delays, errors start, halfway and so on. In other words, the Parkinson's disease is a neurodegenerative disease of elders like Alzheimer's disease and amyotrophic lateral sclerosis. Therefore, Parkinson's disease is gradually replacing the cancer to become one of the causes of death.

Moreover, Parkinson's disease is a chronic disorder of the central nervous system, the causes is still unknown by the medical profession so far. The main symptoms of Parkinson's disease include resting tremor, rigidity, akinesia, bradykinesias, postural instability, poor balance, constipation, slow speech, dull tone and writing to smaller gradually and so on. Parkinson's patients do not only lose the ability to self-control muscles, but also need their families to help and care their daily life, coupled with the reasons that the current health care system is unable to fully cure for Parkinson's disease and patients need long-term observations and treatments, along with the rising of suffering ratio, and the families of the patient and community resources are under a heavy burden. Therefore, how to develop an effective mitigation of suffering due to degeneration of the central nervous system caused by Parkinson's disease has become an anxious technical problem to be solved and improved by the technology industry.

To apply wave energy in sound, electromagnetic or optical form effecting on plant, animal or human, to promote cell growth, or inhibit the growth of foreign cells, or produce specific physiological or psychological treatment or soothing, is currently quite universally endorsed technology and research. But currently available conventional arts are only roughly using a simple fixed frequency wave energy of simply combination of low and high frequencies to act on the human body, they are not in-depth studied to know and have what kind energy wave with controls of combination of specific different frequencies is effective for corresponding diseases and physical discomfort, and they are only rough frequency energy wave regardless what kind illness or physical discomfort to be applied for, so the effectiveness of treatment or relieve of symptoms must be unable to highlight.

Since the biological resonant waves probably have high efficacy in improvement of physiological faculty and curing diseases, and the inventor of the present patent application has researched for a long time to apply the resonant energy wave to improve some kinds of physiological faculty and cure some diseases. The inventor had an invention of system and method for emitting energy wave by specific frequency controls to reduce or eliminate high blood sugar factor of diabetes, and such invention had been issued for Taiwanese patent No. 1453046 and U.S. Pat. No. 9,421,368. After the aforementioned invention, the inventor of the present patent application puts into research applying serial specific controls of energy wave for alleviating or curing diseases such as the present invention for improving the symptoms of the Parkinson's disease.

SUMMARY OF THE INVENTION

The primary objective of the present invention is to provide a system and method for slowing down degeneration of central nervous system caused by Parkinson's disease. The system comprises an energy wave generator including a control unit and an output unit. The control unit includes an energy wave's frequency control mode for controlling and generating energy waves. The energy wave's frequency control mode is set up with multiple controls which operate in multiple energy wave generation periods respectively. According to the multiple controls, the energy wave generator generates and emits energy waves in accordance with multiple base frequencies from 0.5 to 2950 Hz correspondingly to have corresponding multiple energy wave distribution densities (EDs) with values from 0.67 to 7.33 for effecting the bodies of animals or human so as to improve symptoms of Parkinson's disease. The energy wave's frequency control mode comprising at least one fixed frequency sweep mode and at least one adjusted frequency sweep mode. The at least one adjusted frequency sweep mode comprises a sweep decreasing mode, a spread contract mode and/or a sweep increasing mode. The energy wave generator is configured to emit energy waves configured to have a decreasing frequency distribution in a predetermined sweep bandwidth by a predetermined adjusted bandwidth in the sweep decreasing mode, to have a increasing frequency distribution in a predetermined sweep bandwidth by a predetermined adjusted bandwidth in the sweep increasing mode, and to have an increasing frequency distribution and a decreasing frequency distribution alternately in a predetermined sweep bandwidth by a predetermined adjusted bandwidth in the spread contract mode. The energy wave distribution density (ED) of each energy wave is calculated by the following formula: $ED=\log_{10}(freq.\times D\%\times(2Width+1)\times(TT)+1)$, wherein freq., Width, D% and TT represent the base frequency, the predetermined sweep bandwidth, an emission rate and a total time of emission in a duty cycle of the base frequency respectively.

BRIEF DESCRIPTION OF THE DRAWINGS

FIG. 11 is a schematic view of list of relations between spectrums of effect frequencies, modulation parameters and energy densities of the first embodiment of the present invention;

FIG. 12 is a schematic view of list of relations between spectrums of effect frequencies, modulation parameters and energy densities of the second embodiment of the present invention;

DETAILED DESCRIPTION OF THE PREFERRED EMBODIMENT

Referring to FIGS. 1 to 12, the system of the present invention comprises an energy wave generator 10. The energy wave generator 10 is set up with an energy wave's frequency control mode. The energy wave generator 10 generates and emits energy waves (i.e. resonant wave) according to the control of the energy wave's frequency control mode. In one embodiment of the present invention, the energy wave's frequency control mode includes first to sixth sets of controls in corresponding first to sixth sets of energy wave generation periods. The energy wave generator 10 generates and emits the energy waves each with a corresponding energy wave distribution density in accordance with a corresponding frequency sweep mode based on a base frequency in the first to sixth energy wave generation periods respectively according to the controls of the energy wave's frequency control mode, so that the energy waves effect the body of animal or human having Parkinson's disease to slow down degeneration of central nervous system caused by Parkinson's disease.

Figure 1:
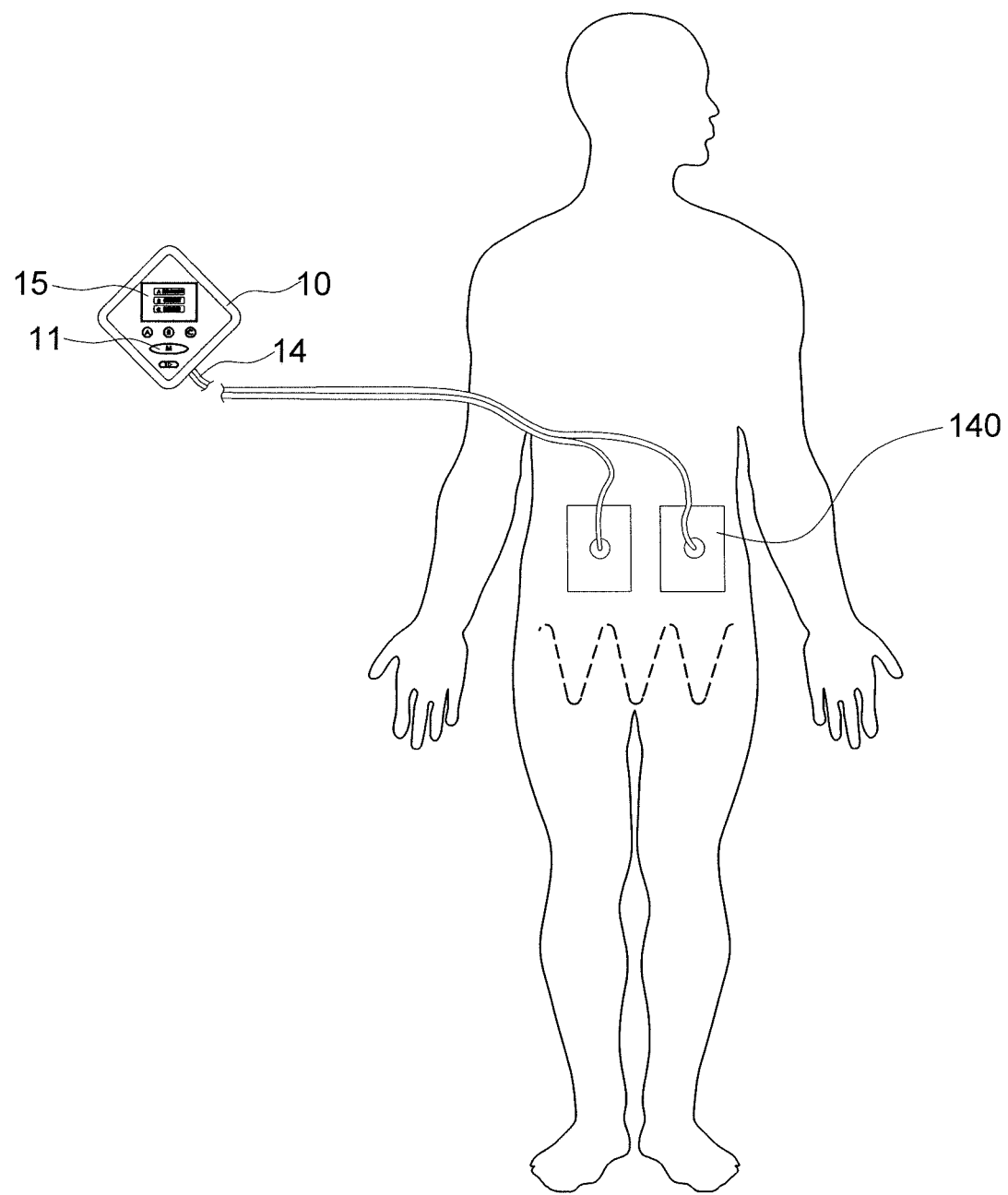
FIG. 1 is a schematic view of the system of the present invention.
Figure 2:
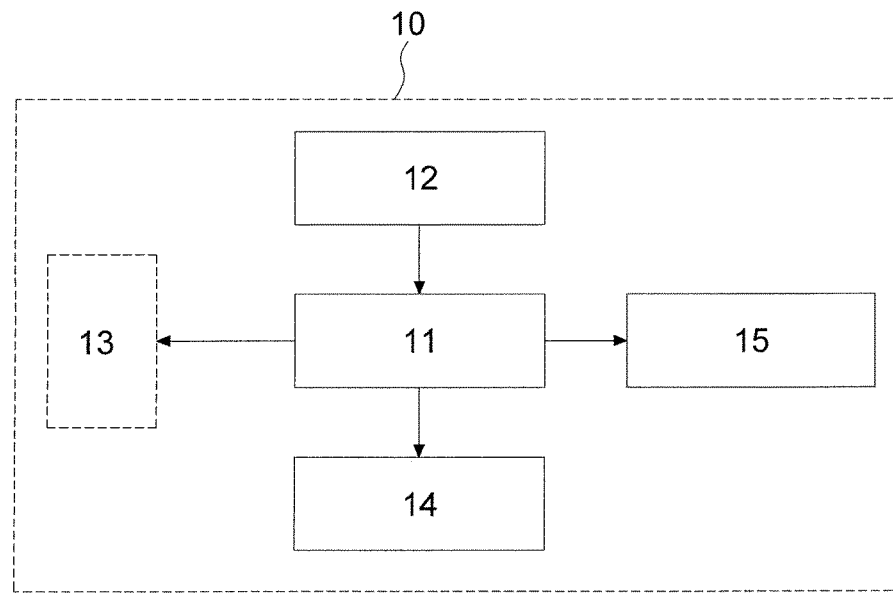
FIG. 2 is a schematic block diagram of units of the system of the present invention.

Referring to FIGS. 1 to 2, the energy wave generator 10 comprises a user interface 11, a control unit 12, a database 13 for saving the information of spectrums of effect frequency and modulation parameters corresponding to each effect frequency used in each energy wave generation periods, an energy wave output unit 14 and a display unit 15. In one embodiment of the present invention, the energy waves are in electric forms, and the energy wave output unit 14 includes a set of electrode sheets 140 for affixing to the body with Parkinson's disease so as to construct a circulation loop between the body and the electrical energy wave output unit 14 to transmit electric energy waves to the body with Parkinson's disease. The control unit 12 (such as a combination of microcontroller and driving circuit) sequentially reads the information of spectrums and modulation parameters of effect frequencies in the database 13, and then drives the energy wave output unit 14 to sequentially generates and emits electric energy waves each with a respective energy wave distribution density (ED) in each corresponding energy wave generation period.

The control unit 12 of the present invention can be triggered to read the associated information of spectrums and modulation parameters in the database 13 by the command signals generated from the user interface 11, and then generates driving signals to control the energy wave output unit 14 (such as weak pulse generating circuit, voltage≤10V, current≤5 mA) switching on and off according to the corresponding frequencies, so that the energy wave output unit 14 generates corresponding electric energy waves with corresponding energy densities in required distributions of values in the corresponding energy wave generation periods. The display unit 15 is used to display the status of operation or procession of the system. Further, the embodiment of the present invention, the energy wave output unit 14 is not to be limited to a weak pulse generating circuit, the energy wave output unit 14 also may be a light emitting device or an audio play device enabling the energy wave generator system 10 to emits energy waves in light form or audio form in required corresponding frequencies.

Referring to FIGS. 3~8 and 11, in a first embodiment of the invention, is useful in the morning, the energy wave generator 10 according to the control of the energy wave's frequency control mode sequentially outputs the energy waves from first to sixth energy wave generation periods. The controls of the energy wave's frequency control mode are for: (a) continuously and sequentially generating a 1st to a 6th energy waves with a corresponding 1st to a 6th energy wave distribution densities (EDs) in accordance with a corresponding 1st to a 6th base frequencies respectively in the first energy wave generation period, wherein, the 1st ED is between 0.67~1.68 (preferably 1.34), the 2nd ED is between 0.82~2.04 (preferably 1.63), the 3rd ED is between 0.90~2.26 (preferably 1.81), the 4th ED is between 0.96~2.41 (preferably 1.93), the 5th ED is between 1.01~2.53 (preferably 2.03) and the 6th ED is between 1.05~2.63 (preferably 2.10); (b) continuously and sequentially generating a 7th to a 11th energy waves with corresponding a 7th to a 11th energy wave distribution densities (EDs) in accordance with a 7th to a 11th base frequencies respectively in the second energy wave generation period, wherein, the 7th ED is between 1.22~3.05 (preferably 2.44), the 8th ED between 1.25~3.12 (preferably 2.50), the 9th ED is between 1.31~3.28 (preferably 2.62), the 10th ED is between 1.36~3.40 (preferably 2.72) and the 11th ED is between 1.40~3.50 (preferably 2.80); (c) continuously and sequentially generating a 12th to a 15th energy waves with a 12th to a 15th energy wave distribution densities (EDs) in accordance with a 12th to a 15th base frequencies respectively in the third energy wave generation period, wherein, the 12th ED is between 1.64~4.10 (preferably 3.28), the 13th ED is between 1.66~4.15 (preferably 3.32), the 14th ED is between 1.72~4.30 (preferably 3.44) and the 15th ED is between 1.8118 4.53 (preferably 3.62); (d) continuously and sequentially generating a 16th to a 19th energy waves with a 16th to a 19th energy wave distribution densities (EDs) in accordance with a 16th to a 19th base frequencies respectively in the fourth energy wave generation period, wherein, the 16th ED is between 2.21~5.53 (preferably 4.42), the 17th ED is between 2.17~5.44 (preferably 4.35), the 18th ED is between 2.15~5.37 (preferably 4.29) and the 19th ED energy-density is between 2.14~5.36 (preferably 4.29); (e) continuously and sequentially generating a 20th to a 22nd energy waves with a 20th to a 22nd energy wave distribution densities (EDs) in accordance with a 20th to a 22nd base frequencies respectively in the fifth energy wave generation period, wherein, the 20th ED is between 1.98~4.94 (preferably 3.95), the 21st ED is between 1.85~4.63 (preferably 5.33) and the 22nd the ED is between 2.07~5.17 (preferably 4.13); (f) continuously and sequentially generating a 23rd to a 29th energy waves with a 23rd to a 29th energy wave distribution densities (EDs) in accordance with a 23rd to a 29th base frequencies respectively in the sixth energy wave generation period, wherein, the 23rd ED is between 1.09~2.73 (preferably 2.18), the 24th ED is between 1.10~2.75 (preferably 2.20), the 25th ED is between 1.08~2.70 (preferably 2.16), the 26th ED is between 1.05~2.61 (preferably 2.09), the 27th ED is between 1.00~2.51 (preferably 2.01), the 28th ED is between 1.00~2.51 (preferably 2.01), and the 29th ED is between 0.74~1.85 (preferably 1.48).

The value of aforementioned energy wave distribution densities (EDs) of the energy waves by their corresponding frequencies are calculated by the formula: $ED=\log_{10}$ (base freq.$\times D\%\times(2\text{Width}+1)\times(TT)+1$). For example of the 1st base frequency in the first energy wave generation period, if we set the 1st base freq.=1 Hz, the emission rate in a duty cycle (D%)=70%, the sweep bandwidth (Width)=0 Hz and the TT=30 secs in a duty cycle, and then the energy wave distribution density $(ED)=\log_{10}$ $(1\times70\%\times(2\times0+1)\times30+1)$ =1.34. Although there is no specific unit referring to the energy wave distribution density (ED) of the present invention, the ED has real meaning, which represents a total transmit power of energy wave. When the frequency is higher, the times of switch voltage (current) is more, and energy used is more. The total time of emission means the duration of effect energy wave. The value of ED has been taken into account with all transmission parameters, which is on behalf of transmitting behavior. If each parameter is changed too large, the ED will also change. If the energy density exceeds the scope of the set ones, the efficiency also will be changed with it.

Figure 3:
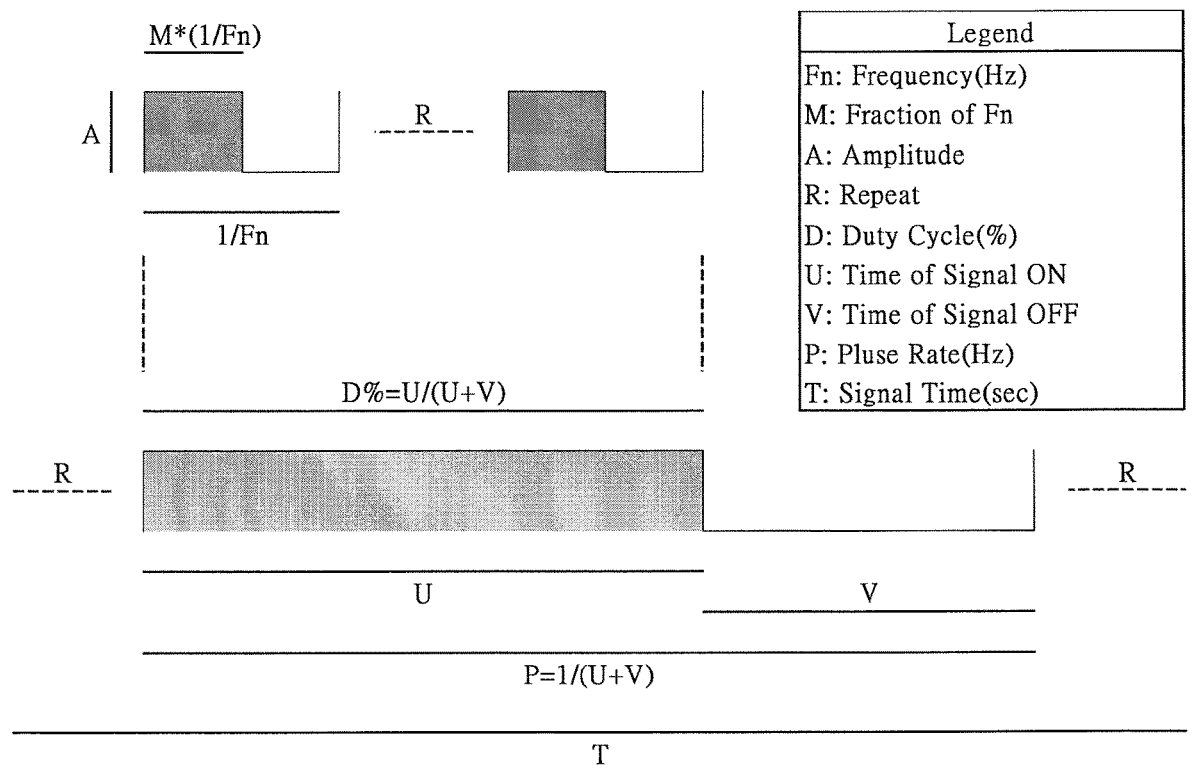
FIG. 3 is a schematic view of wave form of a duty cycle of the present invention.

As shown in FIGS. 3 and 11, in one embodiment of the present invention, the energy wave is a square wave, D is the duty cycle, T is effect time of a single frequency, D% is emission rate of duty cycle of each base frequency and equal to U/(U+V). In the embodiment of present invention, we set the wave emission rate to be 70% for each duty cycle. U is the part of 70% which represents the time of signal outputs of positive potential in square wave, and V is the part of 30% which represents the time of signal outputs of 0 potential in OFF status. P represents a Pluse Rate (Hz) of frequency, $P=1/(U+V)$. TT is the total time of emission period based on each base frequency in each duty cycle. In FIG. 11, the normalized percentages (normal) in each order, is the ratio between the ED in the effect period based on each base frequency and the sum of ED of the whole effect periods based on whole base frequencies from order 1 to 55 shown in FIG. 11.

Referring to FIG. 11, during the first energy wave generation period, the control mode of the 1st frequency is fixed frequency sweep mode, which sets a fixed 1st base frequency within 0.5~10 Hz (preferably 1 Hz), D%=70% for a duty cycle, Width=0 Hz and TT=30 secs for a duty cycle; the control mode of the 2nd frequency is fixed frequency sweep mode, which sets a fixed 2nd base frequency within 1~13 Hz (preferably 2 Hz), D%=70%, Width (m)=0 Hz and TT=30 secs for a duty cycle; the control mode of the 3rd frequency is fixed frequency sweep mode, which sets a fixed 3rd base frequency within 2~13 Hz (preferably 3 Hz), D%=70%, Width=0 Hz and TT=30 secs for a duty cycle; and the control mode of the 4th frequency is fixed frequency sweep mode, which sets a fixed 4th base frequency within 3~8 Hz (preferably 4 Hz), D%=70%, Width=0 Hz and TT=30 secs for a duty cycle; the control mode of the 5th frequency is fixed frequency sweep mode, which sets a fixed 5th base frequency within 4~16 Hz (preferably 5 Hz), D%=70%, Width=0 Hz and TT=30 secs for a duty cycle; and the control mode of the 6th frequency is fixed frequency sweep mode, which sets a fixed 6th base frequency between 5~15 Hz (preferably 6 Hz) with D%=70%, Width=0 Hz and TT=30 secs for a duty cycle.

Referring to FIG. 11, during the second energy wave generation period, the control mode of the 7th frequency is fixed frequency sweep mode, which sets a fixed 7th base frequency between 11~25 Hz (preferably 13 Hz), D%=70%, Width=0 Hz and TT=30 secs for a duty cycle; the control mode of the 8th frequency is fixed frequency sweep mode, which sets a fixed 8th base frequency between 14~22 Hz (preferably 15 Hz), D%=70%, Width=0 Hz and TT=30 secs for a duty cycle; the control mode of the 9th frequency is fixed frequency sweep mode, which sets a fixed 9th base frequency between 18~23 Hz (preferably 20 Hz), D%=70%, Width=0 Hz and TT=30 secs for a duty cycle; and the control mode of the 10th frequency is fixed frequency sweep mode, which sets a fixed 10th base frequency between 23~32 Hz (preferably 25 Hz), D%=70%, Width=0 Hz and TT=30 secs for a duty cycle; and the control mode of the 11th frequency is fixed frequency sweep mode, which sets a fixed 11th base frequency between 28~40 Hz (preferably 30 Hz) with D%=70%, Width=0 Hz and TT=30 secs for a duty cycle.

Referring to FIG. 11, during the third energy wave generation period, the control mode of the 12th frequency is a fixed frequency sweep mode, which sets a fixed 12th base frequency between 85~100 Hz (preferably 90 Hz) with D%=70%, Width=0 Hz and TT=30 secs for a duty cycle; the control mode of the 13th frequency is a fixed frequency sweep mode, which sets a fixed 13th base frequency between 95~105 Hz (preferably 100 Hz) with D%=70%, Width=0 Hz and TT=30 secs for a duty cycle; the control mode of the 14th frequency is a fixed frequency sweep mode, which sets a fixed 14th base frequency between 125~135 Hz (preferably 130 Hz) with D%=70%, Width=0 Hz and TT=30 secs for a duty cycle; the control mode of the 15th frequency is a fixed frequency sweep mode, which sets a fixed 15th base frequency between 195~215 Hz (preferably 200 Hz) with D%=70%, Width=0 Hz and TT=30 secs for a duty cycle.

Referring to FIG. 11, during the fourth energy wave generation period, the control mode of the 16th frequency is a fixed frequency sweep mode, which sets a fixed 16th base frequency between 1350~1370 Hz (preferably 1357 Hz) with D%=70%, Width=0 Hz and TT=28 secs for a duty cycle; the control mode of the 17th frequency is a fixed frequency sweep mode, which sets a fixed 17th base frequency between 1055~1080 Hz (preferably 1062 Hz) with D%=70%, Width=0 Hz and TT=30 secs for a duty cycle; the control mode of the 18th frequency is a fixed frequency sweep mode, which sets a fixed 18th base frequency between 870~890 Hz (preferably 880 Hz) with D%=70%, Width=0 Hz and TT=32 secs for a duty cycle; the control mode of the 19th frequency is a fixed frequency sweep mode, which sets a fixed 19th base frequency between 780~795 Hz (preferably 787 Hz) with D%=70%, Width=0 Hz and TT=35 secs for a duty cycle.

Referring to FIG. 11, during the fifth energy wave generation period, the control mode of the 20th frequency is a fixed frequency sweep mode, which sets a fixed 20th base frequency between 295~315 Hz (preferably 304 Hz) with D%=70%, Width=0 Hz and TT=42 secs for a duty cycle; the control mode of the 21st frequency is a fixed frequency sweep mode, which sets a fixed 21st base frequency between 150~175 Hz (preferably 160 Hz) with D%=70%, Width=0 Hz and TT=45 secs for a duty cycle; the control mode of the 22nd frequency is a sweep decreasing mode, which sets effect frequencies decreasing adjusted and based on a 22nd base frequency between 140~160 Hz (preferably 144 Hz) with D%=70%, Width=2 Hz, adjusted bandwidth=1 Hz and TT=45 secs for a duty cycle. Referring to FIG. 11, during the sixth energy wave generation period, the control mode of the 23rd frequency is a fixed frequency sweep mode, which sets a fixed 23rd base frequency between 6~20 Hz (preferably 9 Hz) with D%=70%, Width=0 Hz and TT=24 secs for a duty cycle; the control mode of the 24th frequency is a fixed frequency sweep mode, which sets a fixed 24th base frequency between 5~15 Hz (preferably 7 Hz) with D%=70%, Width=0 Hz and TT=32 secs for a duty cycle; the control mode of the 25th frequency is a fixed frequency sweep mode, which sets a fixed 25th base frequency between 5~16 Hz (preferably 6 Hz) with D%=70%, Width=0 Hz and TT=34 secs for a duty cycle; the control mode of the 26th frequency is a fixed frequency sweep mode, which sets a fixed 26th base frequency between 3~12 Hz (preferably 5 Hz) with D%=70%, Width=0 Hz and TT=35 secs for a duty cycle; the control mode of the 27th frequency is a fixed frequency sweep mode, which sets a fixed 27th base frequency between 2~15 Hz (preferably 4 Hz) with D%=70%, Width=0 Hz and TT=36 secs for a duty cycle; the control mode of the 28th frequency is a fixed frequency sweep mode, which sets a fixed 28th base frequency between 2~8 Hz (preferably 4 Hz) with D%=70%, Width=0 Hz and TT=36 secs for a duty cycle; the control mode of the 29th frequency is a fixed frequency sweep mode, which sets a fixed 29th base frequency between 0.5~12 Hz (preferably 1 Hz) with D%=70%, Width=0 Hz and TT=42 secs for a duty cycle.

Referring to FIGS. 3~6, 9, 10 and 12, In a second embodiment of the invention, is useful in the afternoon, the energy wave generator 10 according to the control of the energy wave's frequency control mode sequentially outputs the energy waves from first to sixth energy wave generation periods. The controls of the energy wave's frequency control mode are for: (a) continuously and sequentially generating a 1st to a 6th energy waves with a corresponding 1st to a 6th energy wave distribution densities (EDs) in accordance with a corresponding 1st to a 6th base frequencies respectively in the first energy wave generation period, wherein, the 1st ED is between 0.73~4.83 (preferably 1.46), the 2nd ED is between 0.88~2.19 (preferably 1.76), the 3rd ED is between 0.96~2.41 (preferably 1.93), the 4th ED is between 1.03~2.57 (preferably 2.05), the 5th ED is between 1.07~2.69 (preferably 2.15) and the 6th ED is between 1.11~2.78 (preferably 2.23); (b) continuously and sequentially generating a 7th to a 11th energy waves with corresponding a 7th to a 11th energy wave distribution densities (EDs) in accordance with a 7th to a 11th base frequencies respectively in the second energy wave generation period, wherein, the 7th ED is between 1.28~3.20 (preferably 2.56), the 8th ED between 1.31~3.28 (preferably 2.62), the 9th ED is between 1.37~3.44 (preferably 2.75), the 10th ED is between 1.42~3.56 (preferably 2.85) and the 11th ED is between 1.46~3.66 (preferably 2.92); (c) continuously and sequentially generating a 12th to a 15th energy waves with a 12th to a 15th energy wave distribution densities (EDs) in accordance with a 12th to a 15th base frequencies respectively in the third energy wave generation period, wherein, the 12th ED is between 1.49~3.72 (preferably 2.98), the 13th ED is between 1.51~3.78 (preferably 3.02), the 14th ED is between 1.57~3.92 (preferably 3.14) and the 15th ED is between 1.66~4.15 (preferably 3.32); (d) continuously and sequentially generating a 16th to a 19th energy waves with a 16th to a 19th energy wave distribution densities (EDs) in accordance with a 16th to a 19th base frequencies respectively in the fourth energy wave generation period, wherein, the 16th ED is between 2.93~7.33 (preferably 5.87), the 17th ED is between 2.78~6.95 (preferably 5.56), the 18th ED is between 2.73~6.82 (preferably 5.46) and the 19th ED is between 2.67~6.69 (preferably 5.35); (e) continuously and sequentially generating a 20th to a 22nd energy waves with a 20th to a 22nd energy wave distribution densities (EDs) in accordance with a 20th to a 22nd base frequencies respectively in the fifth energy wave generation period, wherein, the 20th ED is between 2.60~6.49 (preferably 5.19), the 21st ED is between 2.58~6.45 (preferably 5.16) and the 22nd the ED is between 2.56~6.41 (preferably 5.13); (f) continuously and sequentially generating a 23rd to a 24th energy waves with a 23rd to a 24th energy wave distribution densities (EDs) in accordance with a 23rd to a 24th base frequencies respectively in the sixth energy wave generation period, wherein, the 23rd ED is between 2.32~5.80 (preferably 4.64) and the 24th ED is between 2.26~5.66 (preferably 4.53).

Referring to FIG. 12, during the first energy wave generation period, the control mode of the 1st frequency is fixed frequency sweep mode, which sets a fixed 1st base frequency within 0.5~10 Hz (preferably 1 Hz), D%=70% for a duty cycle, Width=0 Hz and TT=40 secs for a duty cycle; the control mode of the 2nd frequency is fixed frequency sweep mode, which sets a fixed 2nd base frequency within 1~13 Hz (preferably 2 Hz), D%=70%, Width (m)=0 Hz and TT=40 secs for a duty cycle; the control mode of the 3rd frequency is fixed frequency sweep mode, which sets a fixed 3rd base frequency within 2~13 Hz (preferably 3 Hz), D%=70%, Width=0 Hz and TT=40 secs for a duty cycle; and the control mode of the 4th frequency is fixed frequency sweep mode, which sets a fixed 4th base frequency within 3~8 Hz (preferably 4 Hz), D%=70%, Width=0 Hz and TT=40 secs for a duty cycle; the control mode of the 5th frequency is fixed frequency sweep mode, which sets a fixed 5th base frequency within 4~16 Hz (preferably 5 Hz), D%=70%, Width=0 Hz and TT=40 secs for a duty cycle; and the control mode of the 6th frequency is fixed frequency sweep mode, which sets a fixed 6th base frequency between 5~15 Hz (preferably 6 Hz) with D%=70%, Width=0 Hz and TT=40 secs for a duty cycle.

Referring to FIG. 12, during the second energy wave generation period, the control mode of the 7th frequency is fixed frequency sweep mode, which sets a fixed 7th base frequency between 11~25 Hz (preferably 13 Hz), D%=70%, Width=0 Hz and TT=40 secs for a duty cycle; the control mode of the 8th frequency is fixed frequency sweep mode, which sets a fixed 8th base frequency between 14~22 Hz (preferably 15 Hz), D%=70%, Width=0 Hz and TT=40 secs for a duty cycle; the control mode of the 9th frequency is fixed frequency sweep mode, which sets a fixed 9th base frequency between 18~23 Hz (preferably 20 Hz), D%=70%, Width=0 Hz and TT=40 secs for a duty cycle; and the control mode of the 10th frequency is fixed frequency sweep mode, which sets a fixed 10th base frequency between 23~32 Hz (preferably 25 Hz), D%=70%, Width=0 Hz and TT=40 secs for a duty cycle; and the control mode of the 11th frequency is fixed frequency sweep mode, which sets a fixed 11th base frequency between 28~40 Hz (preferably 30 Hz) with D%=70%, Width=0 Hz and TT=40 secs for a duty cycle.

Referring to FIG. 12, during the third energy wave generation period, the control mode of the 12th frequency is a fixed frequency sweep mode, which sets a fixed 12th base frequency between 85~100 Hz (preferably 90 Hz) with D%=70%, Width=0 Hz and TT=15 secs for a duty cycle; the control mode of the 13th frequency is a fixed frequency sweep mode, which sets a fixed 13th base frequency between 95~105 Hz (preferably 100 Hz) with D%=70%, Width=0 Hz and TT=15 secs for a duty cycle; the control mode of the 14th frequency is a fixed frequency sweep mode, which sets a fixed 14th base frequency between 125~135 Hz (preferably 130 Hz) with D%=70%, Width=0 Hz and TT=15 secs for a duty cycle; the control mode of the 15th frequency is a fixed frequency sweep mode, which sets a fixed 15th base frequency between 195~215 Hz (preferably 200 Hz) with D%=70%, Width=0 Hz and TT=15 secs for a duty cycle.

Referring to FIG. 12, during the fourth energy wave generation period, the control mode of the 16th frequency is a frequency spread contract mode, which sets effect frequencies decreasing and increasing alternately adjusted to contract based on a 16th base frequency between 2800~2950 Hz (preferably 2890 Hz) with D%=70%, Width=5 Hz and TT=33 secs for a duty cycle; the control mode of the 17th frequency is a frequency spread contract mode, which sets effect frequencies decreasing and increasing alternately adjusted to contract based on a 17th base frequency between 1400~1440 Hz (preferably 1422 Hz) with D%=70%, Width =5 Hz, adjusted bandwidth=1 Hz and TT=33 secs for a duty cycle; the control mode of the 18th frequency is a frequency spread contract mode, which sets effect frequencies decreasing and increasing alternately adjusted to contract based on a 18th base frequency between 1100~1150 Hz (preferably 1131 Hz) with D%=70%, Width=5 Hz, adjusted bandwidth=1 Hz and TT=33 secs for a duty cycle; the control mode of the 19th frequency is a frequency spread contract mode, which sets effect frequencies decreasing and increasing alternately adjusted to contract based on a 19th base frequency between 860~890 Hz (preferably 878 Hz) with D%=70%, Width=5 Hz, adjusted bandwidth=1 Hz and TT=33 secs for a duty cycle.

Referring to FIG. 12, during the fifth energy wave generation period, the control mode of the 20th frequency is a frequency spread contract mode, which sets effect frequencies decreasing and increasing alternately adjusted to contract based on a 20th base frequency between 600~625 Hz (preferably 611 Hz) with D%=70%, Width=5 Hz, adjusted bandwidth=1 Hz and TT=33 secs for a duty cycle; the control mode of the 21st frequency is a frequency spread contract mode, which sets effect frequencies decreasing and increasing alternately adjusted to contract based on a 21st base frequency between 565~595 Hz (preferably 573 Hz) with D%=70%, Width=5 Hz, adjusted bandwidth=1 Hz and TT=33 secs for a duty cycle; the control mode of the 22nd frequency is a frequency spread contract mode, which sets effect frequencies decreasing and increasing alternately adjusted to contract based on a 22nd base frequency between 515~540 Hz (preferably 527 Hz) with D%=70%, Width =5 Hz, adjusted bandwidth=1 Hz and TT=33 secs for a duty cycle.

Referring to FIG. 12, during the sixth energy wave generation period, the control mode of the 23rd frequency is a frequency spread contract mode, which sets effect frequencies decreasing and increasing alternately adjusted to contract based on a 23rd base frequency between 160~186 Hz (preferably 171 Hz) with D%=70%, Width=5 Hz, adjusted bandwidth=1 Hz and TT=33 secs for a duty cycle; the control mode of the 24th frequency is a frequency spread contract mode, which sets effect frequencies decreasing and increasing alternately adjusted to contract based on a 24th base frequency between 120-140 Hz (preferably 132 Hz) with D%=70%, Width=5 Hz, adjusted bandwidth=1 Hz and TT=33 secs for a duty cycle.

Referring to FIGS. 3 and 11, the control mode of the fixed frequency sweep mode depicted in the present invention means the frequency of each treatment functioning at a fixed frequency until the total time (TT) of the base frequency effect period ends. In the case of the first energy wave generation period, for example, assuming that the 15th frequency is 200 Hz, then the 15th frequency is fixed at 200 Hz until the total time of the frequency reaches 15 seconds. After that, it goes to the next base frequency effect period, and so on. Because there is no value change of the frequency range for the fixed frequency sweep mode, therefore, the sweep bandwidth is 0 Hz.

Figure 4:
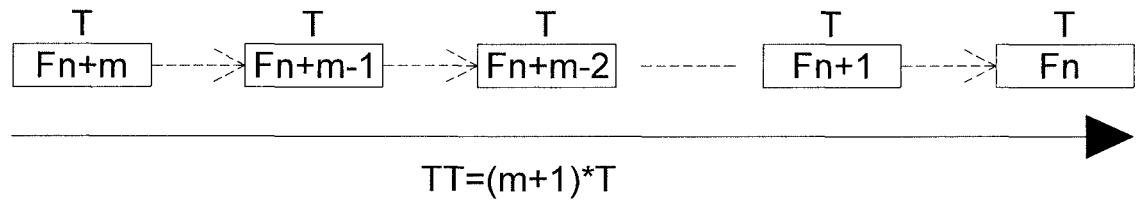
FIG. 4 is a schematic view of distribution of effect frequencies calculated by the sweep decreasing mode of the present invention.
Figure 5:
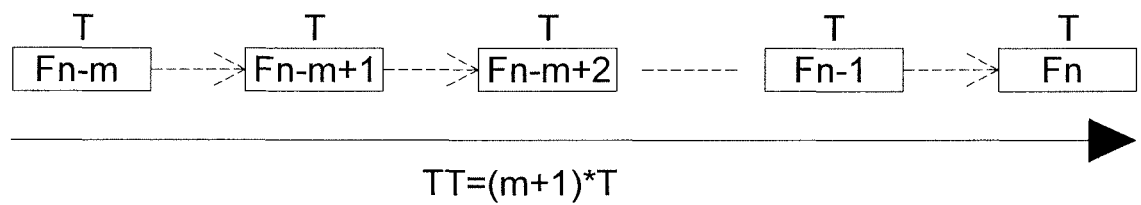
FIG. 5 is a schematic view of distribution of effect frequencies calculated by the sweep increasing mode of the present invention.

Referring to FIGS. 4 and 11, the control mode of the aforementioned frequency sweep decreasing mode is to control the system to emit the energy wave by frequency decreasing distribution with an adjusted bandwidth in the predetermined sweep bandwidth. The calculation of the value change of the sweep decreasing mode depicted in the present invention is described as below. The first output frequency is calculated as a base frequency (Fn) plus a sweep bandwidth (Width), and the second output frequency is calculated as the first output frequency minus an adjusted bandwidth (such as 1 Hz). When the current output frequency is equal to the base frequency (Fn), the current output frequency will be the last output frequency. In the case of the 22nd base frequency of the second embodiment (referring to FIG. 11), for example, the base frequency is 144 Hz with sweep bandwidth (Width) equal to 2 Hz and adjusted bandwidth equal to 1 Hz. Based on the above formula, three frequencies can be obtained, and the sequence of the output effect frequencies are 146 Hz, 145 Hz and 144 Hz respectively. Each single-frequency's effect time (T) in the sweep decreasing mode is 15 seconds, so the total time of the two frequencies (TT) is 45 seconds, i.e., TT=(Width+1)*T.

Figure 6:
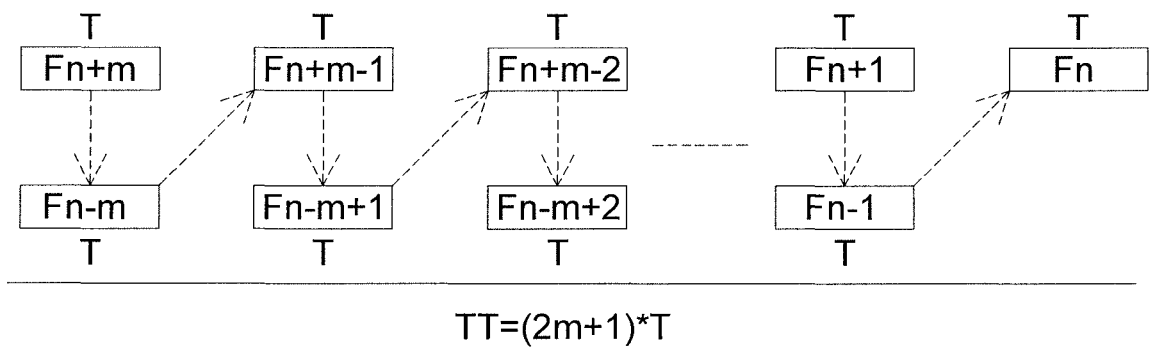
FIG. 6 is a schematic view of distribution of effect frequencies calculated by the spread contract mode of the present invention.

Referring to FIGS. 6 and 12, the control mode of the aforementioned frequency spread contract mode is to control the system to emit the energy wave by alternating increasing frequency and decreasing frequency distribution with an adjusted bandwidth in a predetermined sweep bandwidth. The calculation of the value change of the spread contract mode depicted in the present invention is described as below. The first output frequency is calculated as a base frequency (Fn) minus a sweep bandwidth (Width), the second output frequency is calculated as a base frequency (Fn) plus a sweep bandwidth (Width), the third output frequency is calculated as the first output frequency plus an adjusted bandwidth (such as 1 Hz), the fourth output frequency is calculated as the second output frequency minus an adjusted bandwidth (such as 1 Hz), and so on. When the current output frequency is equal to the base frequency (Fn), the current output frequency will be the last output frequency. In the case of the 16th base frequency, for example, the 16th base frequency is 2890 Hz with the sweep bandwidth (Width)=5 Hz and the adjusted bandwidth=1 Hz. Based on the above formula, eleven frequencies can be obtained, and the sequence of the output effect frequencies are 2895 Hz, 2885 Hz, 2894 Hz, 2886 Hz, 2893 Hz, 2887 Hz, 2892 Hz, 2888 Hz, 2891 Hz, 2889 Hz and 2890 Hz respectively. Each single-frequency's effect time (T) is 3 seconds, so that the total time of the fifteen frequencies (TT) is 33 seconds, i.e., TT=(2Width+1)*T.

Figure 7:
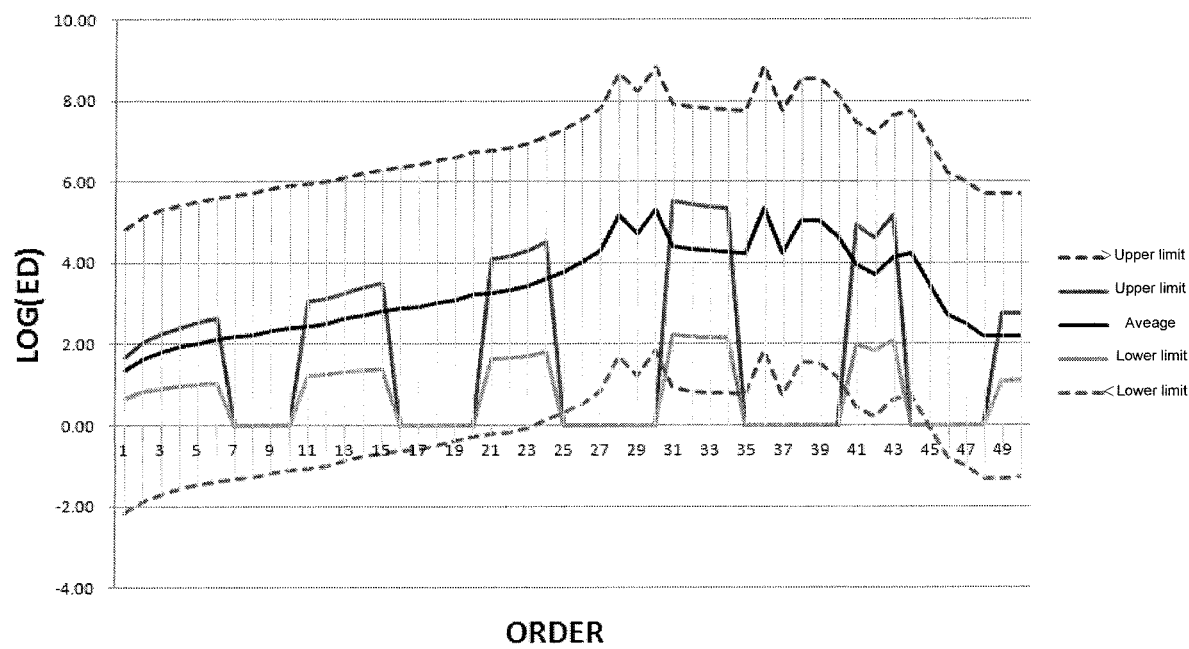
FIG. 7 is a schematic view of distribution of energy density on linear timeline of the first embodiment of the present invention.
Figure 8:
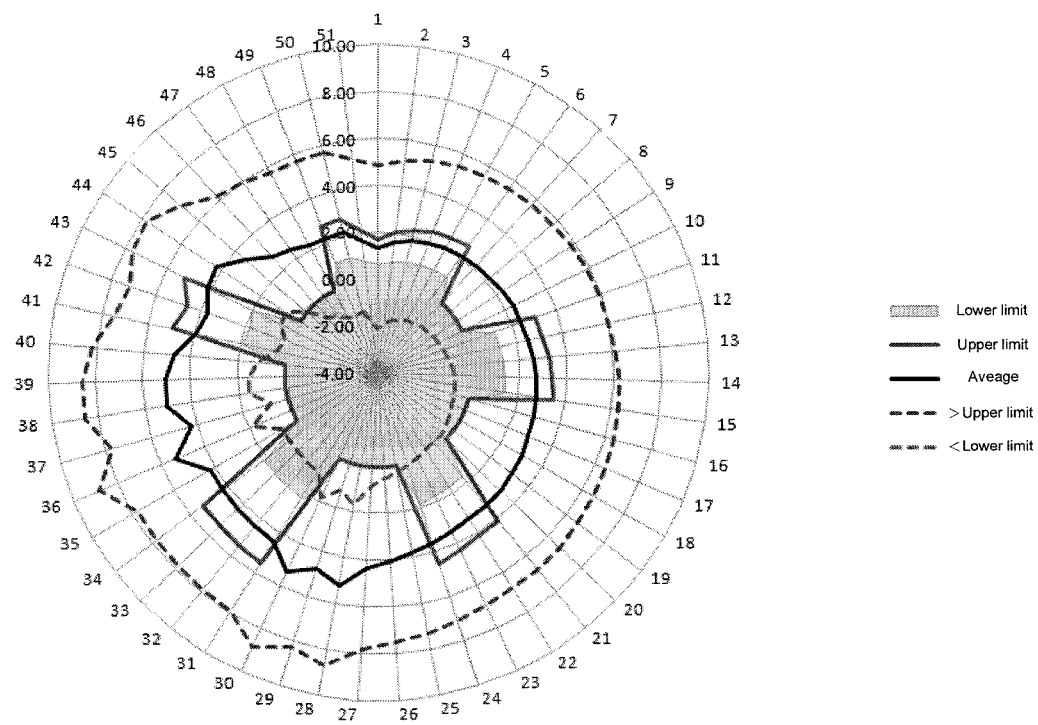
FIG. 8 is a schematic view of distribution of energy density on circular timeline of the first embodiment of the present invention.
Figure 9:
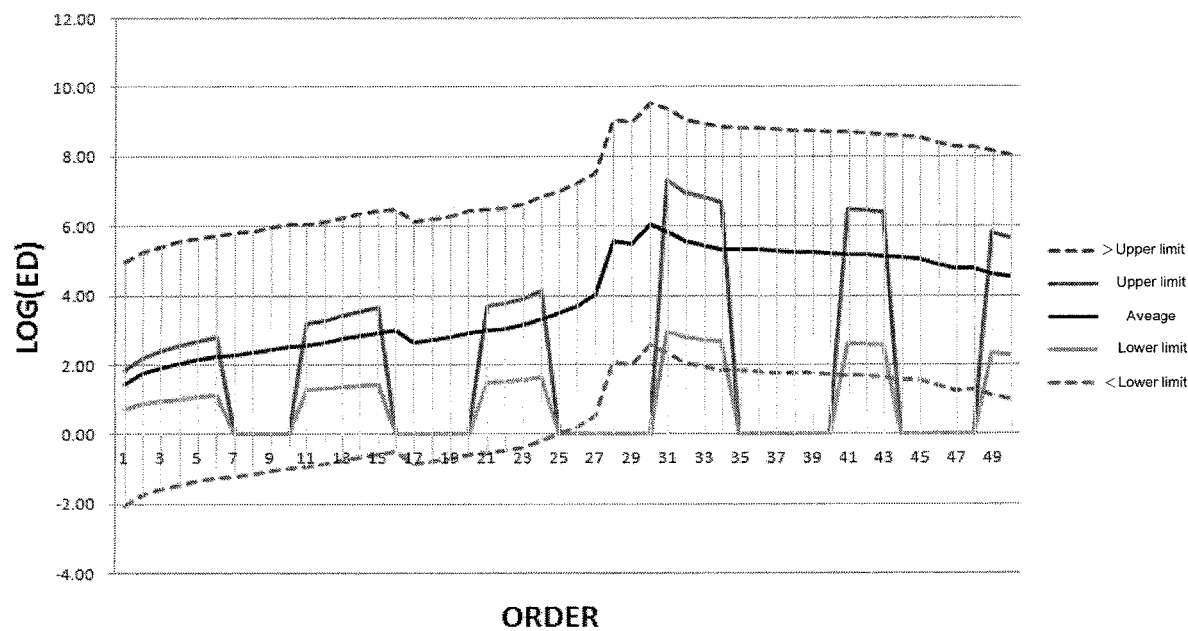
FIG. 9 is a schematic view of distribution of energy density on linear timeline of the second embodiment of the present invention.
Figure 10:
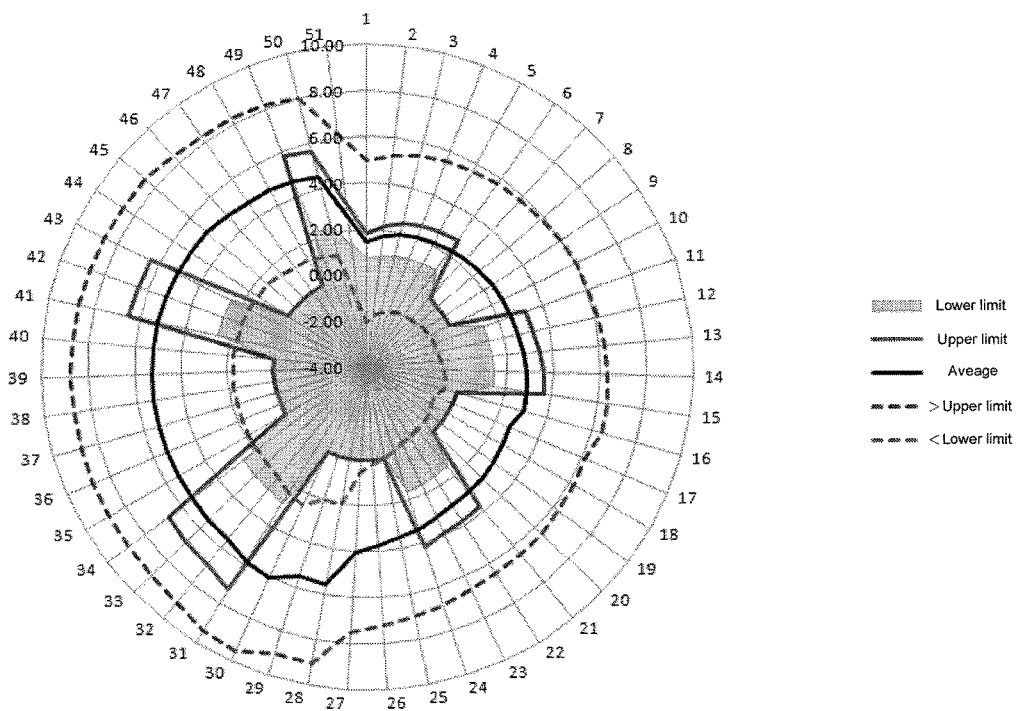
FIG. 10 is a schematic view of distribution of energy density on circular timeline of the second embodiment of the present invention.
Figure 13:
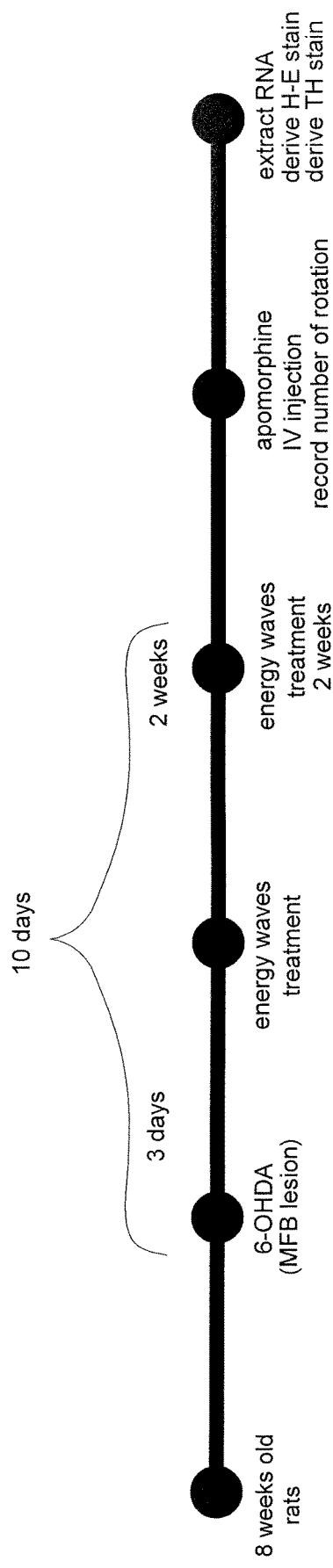
FIG. 13 is a schematic view of flow chart of experiment of the present invention.

FIGS. 7 and 9 show the distribution schematic of the energy density in energy wave's frequency control mode against the linear timeline of the first and second embodiment respectively. Wherein, the upper limit and the lower limit shown in FIGS. 7 and 9 represent the upper range and the lower range of the energy density against the timeline mentioned above in accordance with the present invention. FIGS. 8 and 10 show the distribution schematic of the energy density in energy wave's frequency control mode against the annular timeline of the first and second embodiment respectively, and wherein the central portion is the average distribution of the energy density against the timeline mentioned above in accordance with the present invention.

On the chart shown in FIG. 11 for the first embodiment useful in the morning, the base frequency distributions of first to sixth energy wave generation periods are from orders 1-6, 11-15, 21-24, 31-34, 41-43 and 49-55 chronologically respectively. On the chart shown in FIG. 12 for the second embodiment useful in the afternoon, the base frequency distributions of first to sixth energy wave generation periods are from orders 1-6, 11-15, 21-24, 31-34, 41-43 and 49-50 chronologically respectively.

In the present embodiment, besides above frequency treatment period, the energy wave's frequency control mode also includes five non-energy periods, i.e., from the first to the fifth non-energy periods generated between every two adjacent energy density from the first to the ninth periods correspondingly. The total time of the first to eighth non-energy periods are 120, 150, 155, 199 and 139 seconds for the first embodiment, and 160, 100, 258, 198 and 165 seconds for the second embodiment respectively. The energy wave generator 10 generates various frequencies in each non-energy periods and filters the frequency to have non-energy. Referring to FIGS. 11 and 12, the first to the eighth non-energy periods is chronologically generated in-between order 7-10, order 16-20, order 25-30, order 35-40 and order 44-48 in sequence.

Figure 14:
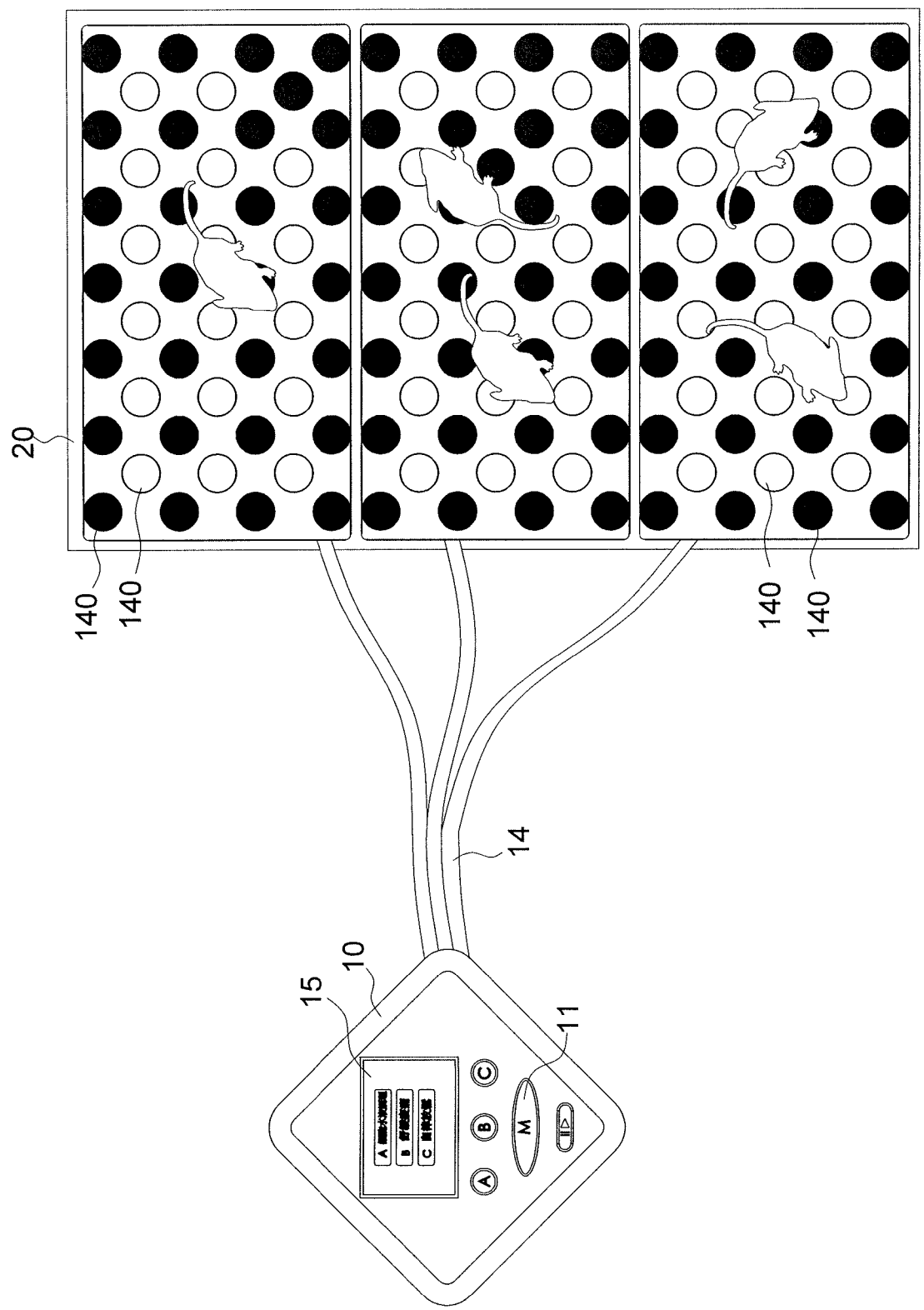
FIG. 14 is a schematic view of experimental device of the present invention.
Figure 15:
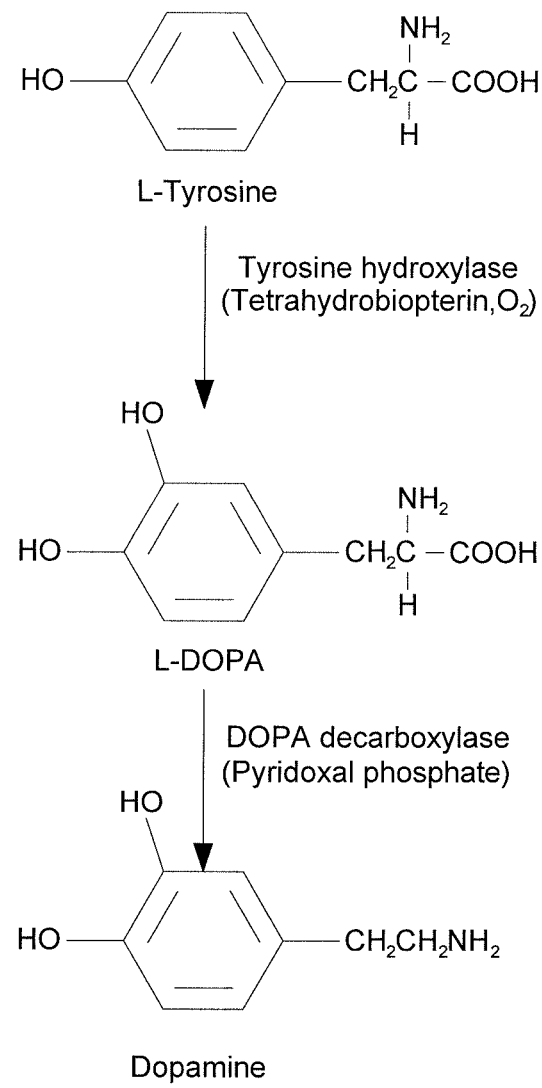
FIG. 15 is a schematic view of synthetizing path of dopamine.
Figure 16:
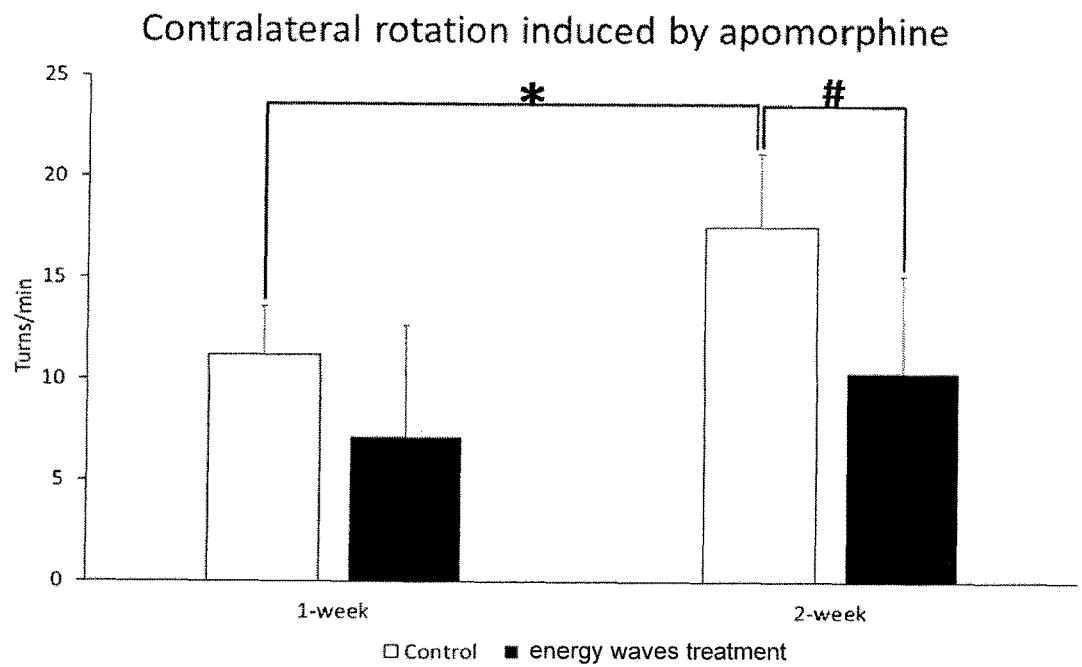
FIG. 16 is a schematic view of comparisons of rotation status of two groups of rats with unilateral induced rotation in first and second weeks respectively of the present invention.
Figure 17:
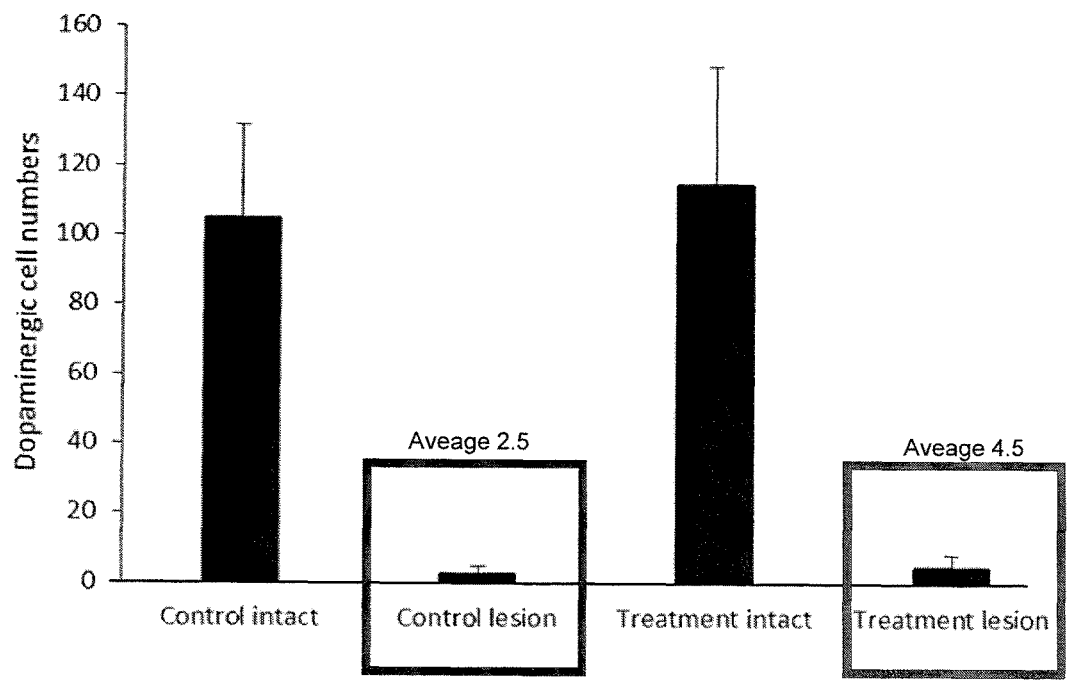
FIG. 17 is a schematic view of comparisons of dopaminergic cell numbers of two groups of rats before and after brain injury of the present invention.

In order to verify the feasibility of the present invention, the inventor has carried out animal experiments, and derived the relevant charts are shown as FIGS. 13-17. First, Referring to FIGS. 13 and 14, we prepared about 8 weeks old rats for induced unilateral (contralateral) rotation experiment. We proceeded with unilateral brain injury treatment (MFB lesion) firstly, then divided the rats into two groups, one group of rats are without resonant energy waves treatment called as control group, and the other group of rats were put on a plate 20 with a plurality of electrode sheet 140 linked with the resonant energy waves generator for the treatment of resonant energy waves for two weeks called as resonant energy waves treatment group (5 times per week, 2 times per day and 30 minutes per time). During these two weeks, these two groups of rats were induced unilateral (contralateral) rotation (apomorphine IV injection) once in each week respectively, and recorded the number of rotations in 20 minutes. Finally, the rats were sacrificed for their organization and extracted their RNA, obtained H-E staining and dopamine TH staining from their tissue sections for subsequent analysis. FIG. 14 shows the rats were placed in the pate 20 with resonant energy waves treatment. FIG. 16 shows the comparison of the rats with unilateral induced (contralateral) rotation experiment. Referring to FIG. 16, these two groups were injected (6-OHDA) about 8 μg/4 μl into middle-forebrain bundle in the first week, and it shows that after one week treatment there is no significant difference between these two groups by using apomorphine-induced contralateral rotation. And after two weeks of treatment, when using apomorphine-induced contralateral rotation, there is a significant difference between the resonant energy waves treatment group and the control group ($p<0.05$,#), and there is a significant difference between one and two week ($p<0.05$,*). Referring to FIG. 17, the average number of dopamine nerve cells of the control group was 104.8, while the average number of unilateral brain injury is 2.5; the average number of dopamine nerve cells of the resonant energy waves treatment is 114.5, while the average number of unilateral brain injury is 4.5. Obviously, the present invention is usable to improve the central nervous system degeneration caused by Parkinson's disease.

While we have shown and described the embodiment in accordance with the present invention, it should be clear to those skilled in the art that further embodiments may be made without departing from the scope of the present invention.

What is claimed is:

1. A system for slowing down degeneration of central nervous system caused by Parkinson's disease, comprising an energy wave generator, the energy wave generator including a control unit and an output unit, the control unit including an energy wave's frequency control mode; the energy wave's frequency control mode comprising multiple sets of controls which operate in multiple energy wave generation periods correspondingly; the output unit including a set of electrode sheets for affixing to a body of animal or human having Parkinson's disease so as to construct a circulation loop between the body and the output unit; the control unit according to the multiple sets of controls configured to control the circulation loop to be switched on and off in accordance with multiple sets of base frequencies to generate multiple sets of energy waves with multiple sets of energy distribution densities (EDs) correspondingly; the multiple sets of energy waves configured to be emitted out by electrode sheets of the output unit configured to effect the body; the energy wave's frequency control mode comprising at least one fixed frequency sweep mode and at least one adjusted frequency sweep mode; the at least one adjusted frequency sweep mode being a sweep decreasing mode, a spread contract mode and/or a sweep increasing mode; the energy wave generator configured to emit energy waves configured to have a decreasing frequency distribution in a predetermined sweep bandwidth by a predetermined adjusted bandwidth in the sweep decreasing mode, to have an increasing frequency distribution in a predetermined sweep bandwidth by a predetermined adjusted bandwidth in the sweep increasing mode, and to have an increasing frequency distribution and a decreasing frequency distribution alternately in a predetermined sweep bandwidth by a predetermined adjusted bandwidth in the spread contract mode; the energy distribution density (ED) of each energy wave being calculated by the following formula: $ED=\log_{10}(freq.\times D\%\times(2Width+1)\times(TT)+1)$, wherein freq., Width, D% and TT represent the base frequency, the predetermined sweep bandwidth, an emission rate and a total time of emission in a duty cycle of the base frequency respectively, wherein, the multiple controls configured to be at least two sets of controls selected from the group consisting of a 1st, a 2nd, a 3rd, a 4th, a 5th and a 6th sets of controls; the multiple energy wave generation periods configured to be at least two of energy wave generation periods selected from the group consisting of a 1st, a 2nd, a 3rd, a 4th, a 5th and a 6th energy wave generation periods which are coordinate with the 1st, a 2nd, a 3rd, a 4th, a 5th and a 6th sets of controls; the multiple sets of energy waves configured to be at least two sets of energy waves selected from the group consisting of a 1st, a 2nd, a 3rd, a 4th, a 5th and a 6th sets of energy waves which are coordinate with the 1st, a 2nd, a 3rd, a 4th, a 5th and a 6th sets of controls; the multiple sets of base frequencies configured to be at least two sets of base frequencies selected from the group consisting of a 1st, a 2nd, a 3rd, a 4th, a 5th and a 6th sets of base frequencies which are coordinate with the 1st, a 2nd, a 3rd, a 4th, a 5th and a 6th sets of controls; the multiple sets of EDs configured to be at least two sets of EDs selected from the group consisting of a 1st, a 2nd, a 3rd, a 4th, a 5th and a 6th sets of EDs which are coordinate with the 1st, a 2nd, a 3rd, a 4th, a 5th and a 6th sets of controls and coordinate with the 1st, a 2nd, a 3rd, a 4th, a 5th and a 6th sets of base frequencies; wherein, the 1st to 6th sets of base frequencies being 0.5~16 Hz, 11~40 Hz, 85~215 Hz, 780~1370 Hz, 140~315 Hz and 0.5~20 Hz correspondingly, and the 1st to 6th sets of EDs being 0.67~2.63, 1.22~3.50, 1.64~4.53, 2.14~5.53, 1.85~5.17 and 0.74~2.75 correspondingly; or wherein, the 1st to 6th sets of base frequencies being 0.5~16 Hz, 11~40 Hz, 85~215 Hz, 860~2950 Hz, 515~625 Hz and 120~180 Hz correspondingly, and the 1st to 6th sets of EDs being 0.73~2.78, 1.28~3.66, 1.49~4.15, 2.67~7.33, 2.56~6.49 and 2.26~5.80 correspondingly.

2. The system as claimed in claim 1, wherein there is a non-energy period between every two adjacent periods of the multiple energy wave generation periods, the total time of the non-energy period is selected from the group consisting of 100, 120, 139, 150, 155, 160, 165, 198, 199 and 258 secs.

3. The system as claimed in claim 1, wherein in the 1st energy wave generation period corresponding to the 1st set of controls, the 1st set of energy waves are sequentially a 1st to a 6th energy waves correspondingly with a 1st to a 6th EDs and in accordance with a 1st to a 6th base frequencies respectively, the 1st ED is 0.67~4.68 or 0.73~1.83 and the 1st base frequency is 0.5~10 Hz, the 2nd ED is 0.82~2.04 or 0.88~2.19 and the 2nd base frequency is 1~13 Hz, the 3rd ED is 0.90~2.26 or 0.96~2.41 and the 3rd base frequency is 2~13 Hz, the 4th ED is 0.96~2.41 or 1.03~2.57 and the 4th base frequency is 3~8 Hz, and the 5th ED is 1.01~2.53 or 1.07~2.69 and the 5th base frequency is 4~16 Hz, and the 6th ED is 1.05~2.63 or 1.11~2.78 and the 6th base frequency is 5~15 Hz; in the 2nd energy wave generation period corresponding to the 2nd set of controls, the 2nd set of energy waves are sequentially a 7th to a 11th energy waves correspondingly with a 7th to a 11th EDs and in accordance with a 7th to a 11th base frequencies respectively, the 7th ED is 1.22~3.05 or 1.28~3.20 and the 7th base frequency is 11~25 Hz, the 8th ED is 1.25~3.12 or 1.31~3.28 and the 8th base frequency is 14~22 Hz, the 9th ED is 1.31~3.28 or 1.37~3.44 and the 9th base frequency is 18~23 Hz, the 10th ED is 1.36~3.40 or 1.42~3.56 and the 10th base frequency is 23~32 Hz, the 11th ED is 1.40~3.50 or 1.46~3.66 and the 11th base frequency is 28~40 Hz; in the 3rd energy wave generation period corresponding to the 3rd set of controls, the 3rd set of energy waves are sequentially a 12th to a 15th energy waves correspondingly with a 12th to a 15th EDs and in accordance with a 12th to a 15th base frequencies respectively, the 12th ED is 1.64~4.10 or 1.49~3.72 and the 12th base frequency is 85~100 Hz, the 13th ED is 1.66~4.15 or 1.51~3.78 and the 13th base frequency is 95~105 Hz, the 14th ED is 1.72~4.30 or 1.57~3.92 and the 14th base frequency is 125~135 Hz, the 15 th ED is 1.81~4.53 or 1.66~4.15 and the 15th base frequency is 195~215 Hz; in the 4th energy wave generation period corresponding to the 4th set of controls, the 4th set of energy waves are sequentially a 16th to a 19th energy waves correspondingly with a 16th to a 19th EDs and in accordance with a 16th to a 19th base frequencies respectively, the 16th ED is 2.21~5.53 or 2.93~7.33 and the 16th base frequency is 1350~1370 Hz or 2800~2950 Hz, the 17th ED is 2.17~5.44 or 2.78~6.95 and the 17th base frequency is 1055~1080 Hz or 1400~1440 Hz, the 18th ED is 2.15~5.37 or 2.73~6.82 and the 18th base frequency is 870~890 Hz or 1100~1150 Hz, the 19th ED is 2.14~5.36 or 2.67~6.69 and the 19th base frequency is 780~795 Hz or 860~890 Hz; in the 5th energy wave generation period corresponding to the 5th set of controls, the 5th set of energy waves are sequentially a 20th to a 22nd energy waves correspondingly with a 20th to a 22nd EDs and in accordance with a 20th to a 22nd base frequencies respectively, the 20th ED is 1.98~4.94 or 2.60~6.49 and the 20th base frequency is 295~315 Hz or 600~625 Hz, the 21st ED is 1.85~4.63 or 2.58~6.56 and the 21st base frequency is 150~175 Hz or 565~595 Hz, the 22nd ED is 2.07~5.17 or 2.56~6.41 and the 22nd base frequency is 140~160 Hz or 515~540 Hz; in the 6th energy wave generation period corresponding to the 6th set of controls, the 6th set of energy waves are sequentially a 23rd to a 29th energy waves correspondingly with a 23rd to a 29th EDs and in accordance with a 23rd to a 29th base frequencies respectively, the 23rd ED is 1.09~2.73 and the 23rd base frequency is 6~20 Hz, the 24th ED is 1.10~2.75 and the 24th base frequency is 5~15 Hz, the 25th ED is 1.08~2.70 and the 25th base frequency is 5~16 Hz, the 26th ED is 1.05~2.61 and the 26th base frequency is 3~12 Hz, the 27th ED is 1.00~2.51 and the 27th base frequency is 2~15 Hz, the 28th ED is 1.00~2.51 and the 28th base frequency is 2~8 Hz, and the 29th ED is 0.74~1.85 and the 29th base frequency is 0.5~12 Hz., or in the 6th energy wave generation period corresponding to the 6th set of controls, the 6th set of energy waves are sequentially a 23rd to a 24th energy waves correspondingly with a 23rd to a 24th EDs and in accordance with a 23rd to a 24th base frequencies respectively, the 23rd ED is 2.32~5.80 and the 23rd base frequency is 160~180 Hz, and the 24th ED is 2.26~5.66 and the 24th base frequency is 120~140 Hz.

4. The system as claimed in claim 3, wherein the control modes based on the 1st to 21st and 23rd to 29th base frequencies are fixed frequency sweep modes respectively, the D%=70%, the Width=0 Hz, and the TT=30, 30, 30, 30, 30, 30, 30, 30, 30, 30, 30, 30, 30, 30, 30, 28, 30, 32, 35, 42, 45, 24, 32, 34, 35, 36, 36 and 42 secs respectively; the control mode based on the 22nd base frequencies is sweep decreasing mode, the D%=70%, the Width=2 Hz, and the TT=45 secs; or the controls based on the 1st to 15th base frequencies are fixed frequency sweep modes respectively, the D%=70%, the Width=0 Hz, and the TT=40, 40, 40, 40, 40, 40, 40, 40, 40, 40, 40, 15, 15, 15, 15 and 15 secs respectively; the controls based on the 16th to 24th base frequencies is spread contract mode, the D%=70%, the Width=5, 5, 5, 5, 5, 5, 5, 5 and 5 Hz respectively, and the TT=33, 33, 33, 33, 33, 33, 33, 33 and 33 secs respectively.

5. The system as claimed in claim 1, wherein multiple frequencies are produced and calculated by one predetermined adjusted bandwidth equal to 1 Hz based on each base frequency in each sweep decreasing mode; multiple frequencies are produced and calculated by one predetermined adjusted bandwidth equal to 1 Hz based on each base frequency in each spread contract mode; multiple frequencies are produced and calculated by one predetermined adjusted bandwidth equal to 1 Hz based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the predetermined adjusted bandwidth, and when a current output frequency of the multiple frequencies is equal to the base frequency, the current output frequency is the last output frequency; in the spread contract mode, the first output frequency of the multiple frequencies is calculated as the base frequency minus the Width, the second output frequency of the multiple frequencies is calculated as a base frequency plus the Width, the third output frequency of the multiple frequencies is calculated as the first output frequency plus the predetermined adjusted bandwidth, the fourth output frequency of the multiple frequencies is calculated as the second output frequency minus the predetermined adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the Width, the second output frequency of the multiple frequencies is calculated as the first output frequency plus the predetermined adjusted bandwidth, and when the current output frequency of the multiple frequencies is equal to the base frequency, the current output frequency is the last output frequency.

6. A system for slowing down degeneration of central nervous system caused by Parkinson's disease, comprising an energy wave generator, the energy wave generator including a database saving information of spectrums and modulation parameters of base frequencies, a control unit and an output unit; the control unit including an energy wave's frequency control mode configured to control and generate energy waves; the energy wave's frequency control mode comprising multiple controls which operate in multiple energy wave generation periods correspondingly; the output unit including a set of electrode sheets for affixing to a body of human having Parkinson's disease so as to construct a circulation loop between the body and the output unit to transmit the energy waves to the body; the multiple controls of the control unit configured to read the information of spectrums and modulation parameters of base frequencies saved in the database to control the circulation loop to be switched on and off by corresponding base frequencies, so that the output unit generates corresponding electric energy waves with corresponding energy distribution densities (EDs) in the corresponding energy wave generation periods; the energy waves configured to be emitted out by electrode sheets of the output unit configured to effect the body; the energy wave's frequency control mode comprising at least one fixed frequency sweep mode and at least one adjusted frequency sweep mode; the at least one adjusted frequency sweep mode being a sweep decreasing mode, a spread contract mode and/or a sweep increasing mode; the energy wave generator configured to emit energy waves configured to have a decreasing frequency distribution in a predetermined sweep bandwidth by a predetermined adjusted bandwidth in the sweep decreasing mode, to have an increasing frequency distribution in a predetermined sweep bandwidth by a predetermined adjusted bandwidth in the sweep increasing mode, and to have an increasing frequency distribution and a decreasing frequency distribution alternately in a predetermined sweep bandwidth by a predetermined adjusted bandwidth in the spread contract mode; the energy distribution density (ED) of each energy wave being calculated by the following formula: ED=$\log_{10}$ (freq.×D%×(2 Width+1)×(TT)+1), wherein freq., Width, D% and TT represent the base frequency, the predetermined sweep bandwidth, an emission rate and a total time of emission in a duty cycle of the base frequency respectively, wherein, the multiple controls configured to comprise a 1st, a 2nd, a 3rd, a 4th, a 5th and a 6th sets of controls; wherein according to the 1st, 2nd, 3rd, 4th, 5th and 6th sets of controls, the energy wave generator in a 1st, a 2nd, a 3rd, a 4th, a 5th and a 6th energy wave generation periods correspondingly configured to generate a 1st, a 2nd, a 3rd, a 4th, a 5th and a 6th sets of energy waves correspondingly in accordance with a 1st, a 2nd, a 3rd, a 4th, a 5th and a 6th sets of base frequencies correspondingly so that the 1st, 2nd, 3rd, 4th, 5th and 6th sets of energy waves have a 1st, a 2nd, a 3rd, a 4th, a 5th and a 6th sets of EDs correspondingly; wherein in the 1st energy wave generation period corresponding to the 1st set of controls, the 1st set of energy waves being sequentially a 1st to a 6th energy waves correspondingly with a 1st to a 6th EDs and in accordance with a 1st to a 6th base frequencies correspondingly, the 1st ED being from 0.67 to 1.68 and the 1st base frequency being from 0.5 to 10 Hz, the 2nd ED being from 0.82 to 2.04 and the 2nd base frequency being from 1 to 13 Hz, the 3rd ED being from 0.90 to 2.26and the 3rd base frequency being from 2 to 13 Hz, the 4th ED being from 0.96 to 2.41 and the 4th base frequency being from 3 to 8 Hz, and the 5lth ED being from 1.01 to 2.53 and the 5th base frequency being from 4 to 16 Hz, and the 6th ED being from 1.05 to 2.63 and the 6th base frequency being from 5 to 15 Hz; in the 2nd energy wave generation period corresponding to the 2nd set of controls, the 2nd set of energy waves being sequentially a 7th to a 11th energy waves correspondingly with a 7th to a 11th EDs and in accordance with a 7th to a 11th base frequencies respectively, the 7th ED being from 1.22 to 3.05 and the 7th base frequency being from 11 to 25 Hz, the 8th ED being from 1.25 to 3.12 and the 8th base frequency being from 14 to 22 Hz, the 9th ED being from 1.31 to 3.28 and the 9th base frequency being from 18 to 23 Hz, the 10th ED being from 1.36 to 3.40 and the 10th base frequency being from 23 to 32 Hz, the 11th ED being from 1.40 to 3.50 and the 11th base frequency being from 28 to 40 Hz; in the 3rd energy wave generation period corresponding to the 3rd set of controls, the 3rd set of energy waves being sequentially a 12th to a 15th energy waves correspondingly with a 12th to a 15th EDs and in accordance with a 12th to a 15th base frequencies respectively, the 12lth ED being from 1.64 to 4.10 and the 12th base frequency being from 85 to 100 Hz, the 13th ED being from 1.66 to 4.15 and the 13th base frequency being from 95 to 105 Hz, the 14th ED being from 1.72 to 4.30 and the 14th base frequency being from 125 to 135 Hz, the 15th ED being from 1.81 to 4.53 and the 15th base frequency being from 195 to 215 Hz; in the 4th energy wave generation period corresponding to the 4th set of controls, the 4th set of energy waves being sequentially a 16th to a 19th energy waves correspondingly with a 16th to a 19th EDs and in accordance with a 16th to a 19th base frequencies respectively, the 16th ED being from 2.21 to 5.53 and the 16th base frequency being from 1350 to 1370 Hz, the 17th ED being from 2.17 to 5.44 and the 17th base frequency being from 1055 to 1080 Hz, the 18th ED being from 2.15 to 5.37 and the 18th base frequency being from 870 to 890 Hz, the 19th ED being from 2.14 to 5.36 and the 19th base frequency being from 780 to 795 Hz; in the 5th energy wave generation period corresponding to the 5th set of controls, the 5th set of energy waves being sequentially a 20th to a 22nd energy waves correspondingly with a 20th to a 22nd EDs and in accordance with a 20th to a 22nd base frequencies respectively, the 20th ED being from 1.98 to 4.94 and the 20th base frequency being from 295 to 315 Hz, the 21st ED being from 1.85 to 4.63 and the 21st base frequency being from 150 to 175 Hz, the 22nd ED being from 2.07 to 5.17 and the 22nd base frequency being from 140 to 160 Hz; in the 6th energy wave generation period corresponding to the 6th set of controls, the 6th set of energy waves being sequentially a 23rd to a 29th energy waves correspondingly with a 23rd to a 29th EDs and in accordance with a 23rd to a 29th base frequencies respectively, the 23rd ED being from 1.09 to 2.73 and the 23rd base frequency being from 6 to 20 Hz, the 24th ED being from 1.10 to 2.75 and the 24th base frequency being from 5 to 15 Hz, the 25th ED being from 1.08 to 2.70 and the 25th base frequency being from 5 to 16 Hz, the 26th ED being from 1.05 to 2.61 and the 26th base frequency being from 3 to 12 Hz, the 27th ED being from 1.00 to 2.51 and the 27th base frequency being from 2 to 15 Hz, the 28th ED being from 1.00 to 2.51 and the 28th base frequency being from 2 to 8 Hz, and the 29th ED being from 0.74 to 1.85 and the 29th base frequency being from 0.5 to 12 Hz.

7. The system as claimed in claim 6, wherein the controls based on the 1st to 21st and 23rd to 29th base frequencies are fixed frequency sweep modes respectively, the D%=70%, the Width=0 Hz, and the TT=30, 30, 30, 30, 30, 30, 30, 30, 30, 30, 30, 30, 30, 30, 30, 28, 30, 32, 35, 42, 45, 24, 32, 34, 35, 36, 36 and 42 secs respectively; the control based on the 22nd base frequencies is sweep decreasing mode, the D%=70%, the Width=2 Hz, and the TT=45 secs.

8. The method as claimed in claim 6, wherein there is a non-energy period between every two adjacent periods of the multiple energy wave generation periods, the total time of the non-energy period is 100, 120, 139, 150, 155, 160, 165, 198, 199 or 258 secs.

9. A system for slowing down degeneration of central nervous system caused by Parkinson's disease, comprising an energy wave generator, the energy wave generator including a control unit and an output unit, the control unit including an energy wave's frequency control mode configured to control and generate energy waves;

the energy wave's frequency control mode comprising multiple controls which operate in multiple energy wave generation periods correspondingly; the output unit including a set of electrode sheets for affixing to a body of human having Parkinson's disease so as to construct a circulation loop between the body and the output unit to transmit the energy waves to the body; the control unit configured to control the circulation loop to be switched on and off according to the multiple controls by corresponding base frequencies, so that the energy wave output unit generates corresponding electric energy waves with corresponding energy distribution densities (EDs) in the corresponding energy wave generation periods; the energy waves configured to be emitted out by electrode sheets of the output unit configured to effect the body; the energy wave's frequency control mode comprising at least one fixed frequency sweep mode and at least one adjusted frequency sweep mode; the at least one adjusted frequency sweep mode being a sweep decreasing mode, a spread contract mode and/or a sweep increasing mode; the energy wave generator configured to emit energy waves configured to have a decreasing frequency distribution in a predetermined sweep bandwidth by a predetermined adjusted bandwidth in the sweep decreasing mode, to have an increasing frequency distribution in a predetermined sweep bandwidth by a predetermined adjusted bandwidth in the sweep increasing mode, and to have an increasing frequency distribution and a decreasing frequency distribution alternately in a predetermined sweep bandwidth by a predetermined adjusted bandwidth in the spread contract mode; the energy distribution density (ED) of each energy wave being calculated by the following formula: $ED=\log_{10}$ (freq. $\times D\% \times (2 Width+1) \times (TT)+1)$, wherein freq., Width, D% and TT represent the base frequency, the predetermined sweep bandwidth, an emission rate and a total time of emission in a duty cycle of the base frequency respectively, wherein, the multiple controls configured to comprise a 1st, a 2nd, a 3rd, a 4th, a 5th and a 6th sets of controls; wherein according to the 1st, 2nd, 3rd, 4th, 5th and 6th sets of controls, the energy wave generator in a 1st, a 2nd, a 3rd, a 4th, a 5th and a 6th energy wave generation periods correspondingly configured to generate a 1st, a 2nd, a 3rd, a 4th, a 5th and a 6th sets of energy waves correspondingly in accordance with a 1st, a 2nd, a 3rd, a 4th, a 5th and a 6th sets of base frequencies correspondingly so that the 1st, 2nd, 3rd, 4th, 5th and 6th sets of energy waves have a 1st, a 2nd, a 3rd, a 4th, a 5th and a 6th sets of EDs correspondingly; wherein in the 1st energy wave generation period corresponding to the 1st set of controls, the 1st set of energy waves being sequentially a 1st to a 6th energy waves correspondingly with a 1st to a 6th EDs and in accordance with a 1st to a 6th base frequencies correspondingly, the 1st ED being from 0.73 to 1.83 and the 1st base frequency being from 0.5 to 10 Hz, the 2nd ED being from 0.88 to 2.19 and the 2nd base frequency being from 1 to 13 Hz, the 3rd ED being from 0.96 to 2.41 and the 3rd base frequency being from 2 to 13 Hz, the 4th ED being from 1.03 to 2.57 and the 4th base frequency being from 3 to 8Hz, and the 5th ED being from 1.07 to 2.69 and the 5th base frequency being from 4 to 16 Hz, and the 6th ED being from 1.11 to 2.78 and the 6th base frequency being from 5 to 15 Hz; in the 2nd energy wave generation period corresponding to the 2nd set of controls, the 2nd set of energy waves being sequentially a 7th to a 11th energy waves correspondingly with a 7th to a 11th EDs and in accordance with a 7th to a 11th base frequencies respectively, the 7th ED being from 1.28 to 3.20 and the 7th base frequency being from 11 to 25 Hz, the 8th ED being from 1.31 to 3.28 and the 8th base frequency being from 14 to 22 Hz, the 9th ED being from 1.37 to 3.44 and the 9th base frequency being from 18 to 23 Hz, the 10th ED being from 1.42 to 3.56 and the 10th base frequency being from 23 to 32 Hz, the 11th ED being from 1.46 to 3.66 and the 11th base frequency being from 28 to 40 Hz; in the 3rd energy wave generation period corresponding to the 3rd set of controls, the 3rd set of energy waves being sequentially a 12th to a 15th energy waves correspondingly with a 12th to a 15lth EDs and in accordance with a 12th to a 15th base frequencies respectively, the 12th ED being from 1.49 to 3.72 and the 12th base frequency being from 85 to 100 Hz, the 13th ED being from 1.51 to 3.78 and the 13th base frequency being from 95 to 105 Hz, the 14th ED being from 1.57 to 3.92 and the 14th base frequency being from 125 to 135 Hz, the 15th ED being from 1.66 to 4.15 and the 15th base frequency being from 195 to 215 Hz; in the 4th energy wave generation period corresponding to the 4th set of controls, the 4th set of energy waves being sequentially a 16th to a 19th energy waves correspondingly with a 16th to a 19th EDs and in accordance with a 16th to a 19th base frequencies respectively, the 16th ED being from 2.93 to 7.33 and the 16th base frequency being from 2800 to 2950 Hz, the 17th ED being from 2.78 to 6.95 and the 17th base frequency being from 1400 to 1440 Hz, the 18th ED being from 2.73 to 6.82 and the 18th base frequency being from 1100 to 1150 Hz, the 19th ED being from 2.67 to 6.69 and the 19th base frequency being from 860 to 890 Hz; in the 5th energy wave generation period corresponding to the 5th set of controls, the 5th set of energy waves being sequentially a 20th to a 22nd energy waves correspondingly with a 20th to a 22nd EDs and in accordance with a 20th to a 22nd base frequencies respectively, the 20th ED being from 2.60 to 6.49 and the 20th base frequency being from 600 to 625 Hz, the 21st ED being from 2.58 to 6.56 and the 21st base frequency being from 565 to 595 Hz, the 22nd ED being from 2.56 to 6.41 and the 22nd base frequency being from 515 to 540 Hz; in the 6th energy wave generation period corresponding to the 6th set of controls, the 6th set of energy waves being sequentially a 23rd to a 24th energy waves correspondingly with a 23rd to a 24th EDs and in accordance with a 23rd to a 24th base frequencies respectively, the 23rd ED being from 2.32 to 5.80 and the 23rd base frequency being from 160 to 180 Hz, and the 24th ED being from 2.26 to 5.66 and the 24th base frequency being from 120 to 140 Hz.

10. The system as claimed in claim 8, wherein the controls based on the 1st to 15th base frequencies are fixed frequency sweep modes respectively, the D%=70%, the Width=0 Hz, and the TT=40, 40, 40, 40, 40, 40, 40, 40, 40, 40, 40, 15, 15, 15 and 15 secs respectively; the controls based on the 16th to 24th base frequencies is spread contract mode, the D%=70%, the Width=5, 5, 5, 5, 5, 5, 5, 5 and 5 Hz respectively, and the TT=33, 33, 33, 33, 33, 33, 33, 33 and 33 secs respectively.

11. The method as claimed in claim 9, wherein there is a non-energy period between every two adjacent periods of the multiple energy wave generation periods, the total time of the non-energy period is 100, 120, 139, 150, 155, 160, 165, 198, 199 or 258 secs.

* * * * *